United States Patent
Lee et al.

(10) Patent No.: US 9,155,471 B2
(45) Date of Patent: Oct. 13, 2015

(54) METHODS AND SYSTEMS FOR SPATIALLY IDENTIFYING ABNORMAL CELLS

(75) Inventors: W. David Lee, Brookline, MA (US); Moungi G. Bawendi, Cambridge, MA (US); Jorge Ferrer, Cambridge, MA (US)

(73) Assignee: Lumicell, Inc'., Wellesley, MA (US)

( * ) Notice: Subject to any disclaimer, the term of this patent is extended or adjusted under 35 U.S.C. 154(b) by 503 days.

(21) Appl. No.: 12/958,058

(22) Filed: Dec. 1, 2010

(65) Prior Publication Data

US 2011/0104071 A1    May 5, 2011

Related U.S. Application Data

(63) Continuation-in-part of application No. 12/788,851, filed on May 27, 2010, now abandoned.

(60) Provisional application No. 61/181,596, filed on May 27, 2009.

(51) Int. Cl.
*A61B 5/00* (2006.01)
*A61K 49/00* (2006.01)
*A61B 19/00* (2006.01)

(52) U.S. Cl.
CPC .............. *A61B 5/0071* (2013.01); *A61B 5/0084* (2013.01); *A61B 5/415* (2013.01); *A61B 5/418* (2013.01); *A61B 19/5225* (2013.01); *A61K 49/0032* (2013.01); *A61B 5/0086* (2013.01); *A61B 5/0091* (2013.01); *A61B 5/4519* (2013.01); *A61B 2019/5231* (2013.01)

(58) Field of Classification Search
CPC .... A61B 5/0071; A61B 5/0084; A61B 5/418; A61B 19/5225; A61B 5/415; A61B 5/0086; A61B 5/0091; A61B 5/4519; A61B 2019/5231; A16K 49/0032
USPC .......................................................... 424/9.6
See application file for complete search history.

(56) References Cited

U.S. PATENT DOCUMENTS

| | | | |
|---|---|---|---|
| 5,268,486 A | 12/1993 | Waggoner et al. | |
| 5,366,860 A | 11/1994 | Bergot et al. | |
| 5,438,989 A | 8/1995 | Hochman et al. | |
| 5,569,587 A | 10/1996 | Waggoner | |
| 5,593,658 A | 1/1997 | Bogdanov et al. | |
| 5,688,221 A | 11/1997 | Yabe et al. | |
| 5,769,791 A | 6/1998 | Benaron et al. | |
| 5,800,995 A | 9/1998 | Patonay et al. | |
| 5,968,479 A | 10/1999 | Ito et al. | |
| 6,027,709 A | 2/2000 | Little et al. | |
| 6,083,486 A | 7/2000 | Weissleder et al. | |
| 6,136,612 A | 10/2000 | Della Ciana et al. | |
| 6,180,086 B1 | 1/2001 | Achilefu et al. | |
| 6,256,530 B1 | 7/2001 | Wolfe | |
| 6,485,413 B1 | 11/2002 | Boppart et al. | |
| 6,592,847 B1 | 7/2003 | Weissleder et al. | |
| 6,620,621 B1 | 9/2003 | Cohenford et al. | |
| 6,631,230 B1 | 10/2003 | Campbell | |
| 6,667,159 B1 | 12/2003 | Walt et al. | |
| 6,737,247 B2 | 5/2004 | Bogdanov et al. | |
| 6,834,238 B1 | 12/2004 | Hochman | |
| 7,128,894 B1 | 10/2006 | Tannous et al. | |
| 7,285,089 B2 | 10/2007 | Viellerobe et al. | |
| 7,383,076 B2 | 6/2008 | Ntziachristos et al. | |
| 7,383,077 B2 | 6/2008 | Zeng | |
| 7,452,727 B2 | 11/2008 | Hennig et al. | |
| 7,498,029 B2 | 3/2009 | Hasan et al. | |
| 8,815,214 B2 * | 8/2014 | Rajopadhye et al. | 424/9.6 |
| 2002/0064794 A1 | 5/2002 | Leung et al. | |
| 2002/0115862 A1 | 8/2002 | Czerney et al. | |
| 2002/0165456 A1 | 11/2002 | Canpolat et al. | |
| 2003/0039741 A1 | 2/2003 | Carver et al. | |
| 2003/0044353 A1 | 3/2003 | Weissleder et al. | |
| 2003/0138378 A1 | 7/2003 | Hashimshony | |
| 2004/0015062 A1 | 1/2004 | Ntziachristos et al. | |
| 2004/0071332 A1 | 4/2004 | Bruce et al. | |
| 2004/0253593 A1 * | 12/2004 | Cai et al. | 435/6 |
| 2005/0130167 A1 | 6/2005 | Bao et al. | |
| 2005/0171434 A1 | 8/2005 | Madden et al. | |
| 2005/0207668 A1 | 9/2005 | Perchant et al. | |
| 2005/0214221 A1 | 9/2005 | Poss et al. | |
| 2006/0188797 A1 | 8/2006 | Roy et al. | |
| 2006/0253107 A1 | 11/2006 | Hashimshony et al. | |
| 2007/0036725 A1 | 2/2007 | Bogyo et al. | |
| 2007/0160279 A1 | 7/2007 | Demos | |
| 2007/0179174 A1 | 8/2007 | Bachurin et al. | |
| 2007/0182959 A1 | 8/2007 | Maier et al. | |
| 2007/0255169 A1 | 11/2007 | Hashimshony et al. | |

(Continued)

FOREIGN PATENT DOCUMENTS

EP    1065250 A1    1/2001
EP    1211294 A1    6/2002

(Continued)

OTHER PUBLICATIONS

Anikijenko et al., J. Invest. Dermatol., 2001, 117(6), p. 1442-1448.*
Hsiung et al., Nature Med., 2008, 14(4), p. 454-458.*
Palen et al., Peptides, 1987, 8(1), p. 21-24 (abstract).*
International Search Report and Written Opinion for PCT/US2011/062527 mailed Jun. 15, 2012.
International Search Report and Written Opinion for PCT/US2010/036433 mailed Sep. 6, 2010.
International Preliminary Report on Patentability for PCT/US2010/036433 mailed Dec. 8, 2011.
Office Communication mailed Oct. 23, 2012 for U.S. Appl. No. 12/788,851.
Funovics et al., Protease sensors for bioimaging. Anal Bioanal Chem. Nov. 2003;377(6):956-63. Epub Sep. 3, 2003.
Blum et al., "Noninvasive optical imaging of cysteine protease activity using fluorescently quenched activity-based probes", *Nature Chem. Biol.*, 3(10):668-677 (2007).

(Continued)

*Primary Examiner* — Michael G Hartley
*Assistant Examiner* — Leah Schlientz
(74) *Attorney, Agent, or Firm* — Wolf, Greenfield & Sacks, P.C.

(57) ABSTRACT

The present invention provides compositions and methods for imaging tumor resections.

26 Claims, 14 Drawing Sheets

(56) References Cited

U.S. PATENT DOCUMENTS

| | | |
|---|---|---|
| 2007/0260156 A1 | 11/2007 | Hashimshony |
| 2008/0015446 A1 | 1/2008 | Mahmood et al. |
| 2008/0029711 A1 | 2/2008 | Viellerobe et al. |
| 2008/0039742 A1 | 2/2008 | Hashimshony et al. |
| 2008/0076674 A1 | 3/2008 | Litman et al. |
| 2008/0103373 A1 | 5/2008 | Matter et al. |
| 2008/0154102 A1 | 6/2008 | Frangioni et al. |
| 2008/0193373 A1 | 8/2008 | Stritzker et al. |
| 2008/0193431 A1 | 8/2008 | Zheng et al. |
| 2008/0260646 A1 | 10/2008 | Keller et al. |
| 2008/0287750 A1 | 11/2008 | Hashimshony et al. |
| 2009/0004116 A1 | 1/2009 | Bhaumik et al. |
| 2009/0028788 A1 | 1/2009 | Achilefu |
| 2009/0123381 A1 | 5/2009 | Hsieh et al. |
| 2009/0299196 A1 | 12/2009 | Bawendi et al. |
| 2010/0189658 A1 | 7/2010 | Wendt et al. |
| 2010/0286044 A1 | 11/2010 | Litman et al. |
| 2010/0298554 A1 | 11/2010 | Laikhter et al. |
| 2011/0021908 A1 | 1/2011 | Lee et al. |
| 2012/0150164 A1 | 6/2012 | Lee et al. |
| 2014/0207126 A1 | 7/2014 | Bianchi |
| 2014/0207129 A1 | 7/2014 | Lee |
| 2014/0243934 A1 | 8/2014 | Vo-Dinh et al. |
| 2014/0276103 A1 | 9/2014 | Lee et al. |

FOREIGN PATENT DOCUMENTS

| | | |
|---|---|---|
| EP | 1223197 A2 | 7/2002 |
| EP | 1273584 A1 | 1/2003 |
| WO | WO-9713810 A1 | 4/1997 |
| WO | WO-9847538 A2 | 10/1998 |
| WO | WO-0053678 A1 | 9/2000 |
| WO | WO-0190253 A1 | 11/2001 |
| WO | WO-0224815 A1 | 3/2002 |
| WO | WO 02/056670 A2 | 7/2002 |
| WO | WO-03105814 A1 | 12/2003 |
| WO | WO 2008/088865 A2 | 7/2008 |

OTHER PUBLICATIONS

Bogdanov, Jr. et al., "Long-circulating blood pool imaging agents", *Adv. Drug Del. Rev.*, 16:335-348 (1995).

Freireich et al., "Quantitative Comparison of Toxicity of Anticancer Agents in Mouse, Rat, Hamster, Dog, Monkey, and Man", *Cancer Chemother. Rep.*, 50(4):219-244 (1966).

Geigy Pharmaceuticals, "Body Surface Area of Adults", in *Scientific Tables*, Diem and Lentner, Ed., Ciba-Geigy Ltd., Ardsley, New York, p. 537 (1970).

Hart et al., "Cell Binding and Internalization by Filamentous Phage Displaying a Cyclic ArgGly-Asp-containing Peptide", *J. Biol. Chem.*, 269(17):12468-12474 (1994).

Holland et al., "Biodegradable Polymers", *Advances in Pharmaceutical Sciences*, 6:101-164 (1992).

Licha et al., "Synthesis and characterization of cyanine dyes as contrast agents for near-infrared imaging", *SPIE*, 2927:192-198 (1996).

Lin et al., "Novel Near-Infrared Cyanine Fluorochromes: Synthesis, Properties, and Bioconjugation", *Bioconj. Chem.*, 13:605-610 (2002).

Mahmood et al., "Near-Infrared Optical Imaging of Protease Activity for Tumor Detection", *Radiology*, 213:866-870 (1999).

Moats et al., "A 'Smart' Magnetic Resonance Imaging Agent That Reports on Specific Enzymatic Activity", *Angew. Chem. Int. Ed. Engl.*, 36(7):726-728 (1997).

Negrin et al., "In vivo-in vitro study of biodegradable methadone delivery systems", *Biomaterials*, 22(6):563-570 (2001).

Poul et al., "Selection of Tumor-Specific Internalizing Human Antibodies from Phage Libraries", *J. Mol. Biol.*, 301:1149-1161 (2000).

Railton et al., "Myocardial scintigraphy with 1-123 heptadecanoic acid as a test for coronary heart disease", *Euro. J. NucL Med.*, 13:63-66 (1987).

Tyagi et al., "Multicolor molecular beacons for allele discrimination", *Nat. Biotechnol.*, 16:49-53 (1998).

van Eenige et al., "Clinical value of studies with radioiodinated heptadecanoic acid in patients with coronary artery disease", *Eur. Heart J.*, 11:258-268 (1990).

Weissleder et al., "In vivo imaging of tumors with protease-activated near-infrared fluorescent probes", *Nat. Biotechnol.*, 17:375-378 (1999).

Weissleder et al., "In vivo magnetic resonance imaging of transgene expression", *Nat. Med.*, 6(3):351-354 (2000).

Zaheer et al., "In vivo near-infrared fluorescence imaging of osteoblastic activity", *Nature Biotech.*, 19:1148-1154 (2001).

Extended European Search Report for European Application No. 11844820.8 dated Jul. 15, 2014.

International Preliminary Report on Patentability for PCT/US2011/062527 mailed Jun. 13, 2013.

International Search Report and Written Opinion for PCT/US2014/027287 mailed Jul. 18, 2014.

Invitation to Pay Additional Fees for PCT/US2014/027769 mailed Aug. 14, 2014.

Bigio et al., Diagnosis of breast cancer using elastic-scattering spectroscopy: preliminary clinical results. J Biomed Opt. Apr. 2000;5(2):221-8.

Demos et al., Near-infrared autofluorescence imaging for detection of cancer. J Biomed Opt. May-Jun. 2004;9(3):587-92.

Goldberg et al., Radiofrequency tissue ablation: importance of local temperature along the electrode tip exposure in determining lesion shape and size. Acad Radiol. Mar. 1996;3(3):212-8.

Holsinger et al., Use of the photonic band gap fiber assembly CO2 laser system in head and neck surgical oncology. Laryngoscope. Jul. 2006;116(7):1288-90.

Kong et al., Comparative analysis of different laser systems to study cellular responses to DNA damage in mammalian cells. Nucleic Acids Res. May 2009;37(9):e68. doi: 10.1093/nar/gkp221. Epub Apr. 7, 2009.

Mullenix et al., Secondary operations are frequently required to complete the surgical phase of therapy in the era of breast conservation and sentinel lymph node biopsy. Am J Surg. May 2004;187(5):643-6.

Reinisch, Laser physics and tissue interactions. Otolaryngol Clin North Am. Dec. 1996;29(6):893-914.

Rogakou et al., Megabase chromatin domains involved in DNA double-strand breaks in vivo. J Cell Biol. Sep. 6, 1999;146(5):905-16.

Tung et al., In vivo imaging of proteolytic enzyme activity using a novel molecular reporter. Cancer Res. Sep. 1, 2000;60(17):4953-8.

Vaidya et al., Intraoperative T staging in radical retropubic prostatectomy: is it reliable? Urology. May 2001;57(5):949-54.

Vogel et al., Mechanisms of pulsed laser ablation of biological tissues. Chem Rev. Feb. 2003;103(2):577-644.

Zornig et al., Re-excision of soft tissue sarcoma after inadequate initial operation. Br J Surg. Feb. 1995;82(2):278-9.

\* cited by examiner

METHODS AND SYSTEMS FOR SPATIALLY IDENTIFYING ABNORMAL CELLS

RELATED APPLICATIONS

This application is a continuation in part of U.S. Ser. No. 12/788,851, filed May 27, 2010 and claims the priority benefit of provisional application U.S. Ser. No. 61/181,596 filed May 27, 2009, the contents of which are herein incorporated by reference in its entirety.

FIELD OF THE INVENTION

The present invention relates generally to the identification of cancer cells during surgical procedures.

BACKGROUND OF THE INVENTION

Molecular imaging can be broadly defined as the characterization and measurement of biological processes at the cellular and molecular level in mammals and human patients. In contradistinction to "classical" diagnostic imaging, for example, magnetic resonance (MR), computed tomography (CT), and ultrasound (US) imaging, molecular imaging analyzes molecular abnormalities that are the basis of disease, rather than imaging the end-effects of these molecular alterations. Specific imaging of molecular targets allows earlier detection and characterization of disease, as well as earlier and direct molecular assessment of treatment efficacy. Molecular imaging can theoretically be performed with different imaging technologies, up to now preferably with nuclear imaging technologies, (e.g., PET and SPECT imaging) which have high sensitivity of probe detection. The IV administered imaging probes typically recognize a given target. Alternatively, some probes detectable by MR imaging have been developed (Moats et al., Angewandte Chemie Int. Ed., 36:726-731, 1997; Weissleder et al., Nat. Med., 6:351-5, 2000), although their detection threshold is generally in the micromolar instead of the pico/femtomolar range of isotope probes.

An alternative molecular imaging method is to use fluorescent probes for target recognition. For example, enzyme activatable fluorochrome probes are described in Weissleder et al., U.S. Pat. No. 6,083,486, and fluorescent molecular beacons that become fluorescent after DNA hybridization are described in Tyagi et al. (Nat. Biotechnol., 16:49-53, 1998). Fluorescent activatable probes have been used to label specific tissue for in vitro culture and histologic sections and are detected using fluorescence microscopy. When administered in vivo, fluorescent activatable probes have been detected by surface-weighted reflectance imaging (Weissleder et al., Nat. Biotechnol., 17:375-8, 1999); (Mahmood et al., Radiology, 213:866-70, 1999).

A need exists to be able to detect molecular imaging probes at or near the surface of exposed tissue during surgery, without confocal microscopy and related limitations on the field of view and depth of focus. Such methods and systems could be used in clinical settings to guide surgery or therapy when localization of the target is important for treatment, such as for example in cancer treatment. The ability to detect single cells marked by probes would guide the surgery of tumor removal. A surgeon could scan the resection area to determine if all of the cancer has been removed during the surgery which could provide a level of effectiveness that could not otherwise be achieved. Should the surgeon remove all cancerous cells upon the initial surgery, further cancer recurrence could be mitigated or avoided and adjuvant treatments could be reduced or eliminated (e.g. followup surgeries, radiation therapy, chemotherapy, etc.) resulting in reduced patient discomfort, morbidity, and significant cost savings to the healthcare system.

SUMMARY OF THE INVENTION

We have developed a system which uses visible light wavelengths to excite and detect a molecular fluorescence probe selectively activated by abnormal cells for use during surgical procedures. The probe and imaging device have been optimized for imaging tissue at depths less than about 1 cm from the exposed surface. Furthermore, the probe has been optimized for surgical procedure times of less than about 2 hours or between about 12 and 36 hours post-administration of the probe.

In one aspect, the invention provides a method for spatially determining tissue heterogeneity in a subject undergoing surgery or a minimally invasive intervention by administering a composition comprising a molecular imaging probe to the subject and obtaining an in situ image of the tissue. The image allows for the detection of a diseased cell, if present in the tissue.

In another aspect the invention provides a method of tumor resection by administering a composition comprising a molecular imaging probe to a tissue of a subject undergoing surgery or a minimally invasive intervention, obtaining an in situ image of the tissue where the image allows for the detection of a diseased cell, if present in the tissue, removing the diseased cell detected and repeating the imaging and removing step until no diseased cell is detected in the tissue.

In a further aspect the invention provides a method of confirming the surgical margin of an excised tumor or growth by topically administering a composition comprising a molecular imaging probe to the surface of the excised tumor or growth and obtaining an in situ image of the tumor or growth where the image allows for the detection of a diseased cell, if present in the tissue.

The molecular imaging probe is administered systemically to the subject or alternatively topically to the tissue. Topical administration includes for example spraying or painting. The molecular imaging probe diffuses into the tissue in less than 5 minutes after topical administration. Optionally the molecular imaging probe is administered on a film or sponge. Preferably, the molecular imaging probe is actvated by the tumor.

The diseased cell is a tumor cell.

In some aspects the molecular imaging probe contains a targeting moiety and an imaging moiety. An imaging moiety includes for example a chromophore, a fluorochrome or a chemoluminescent moiety. The fluorochrome is a visible light or "far red" fluorochrome such as Cy3, Cy3.5, Cy5, Alexa 568, Alexa 546, Alexa 610, Alexa 647, ROX, TAMRA, Bodipy 576, Bodipy 581, Bodipy TR, Bodipy 630, VivoTag 645, and Texas Red. The chemoluminescent moiety is a bioluminescent moietycombining luciference and luciferin, Guassia luciferase and colenterazine, or luminol and peroxide.

In some aspects the targeting moiety binds specifically to CD20, CD33, carcinoembryonic antigen (CEA), alpha fetoprotein (AFP), CA125, CA19-9, prostate specific antigen (PSA), human chorionic gonadotropin (HCG), acid phosphatase, neuron specific enolase, galacatosyl transferase II, immunoglobulin, CD326, her2NEU, EGFR, PSMA, TTF1, Muc, immature glycoslytaion, or an EMT marker.

Optionally the composition comprising the molecular imaging probe further conatins a UV dye, a fluorescent compound, or a compound which alters the osmotic pressure, the pH, or ionic strength at the site of administration.

The probe is constructed of one or more fluorochromes quenched by each other or quenched through the use of dark quencher molecules, attached together with an enzyme activation site and a pharmacokinetic modifier. Importantly, the pharmacokinetic modifier is adjusted to optimize the administration-to-imaging time spread. After cleavage of the enzyme activation site, the fluorochromes and quenchers are spatially separated allowing fluorescence excitation and detection of the fluorochromes.

The probe fluorochrome is chosen from a group of available compounds in the 350-670 nm visible spectrum to preferentially image cells at or near the tissue surface while ignoring deep tissue emission.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

Figure 1:
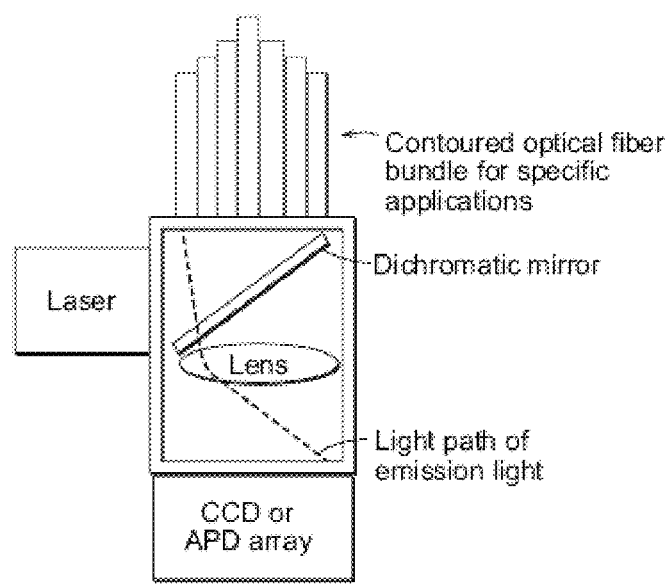
FIG. 1 is a schematic showing a fiber bundle, dichromatic mirror and lens configuration of the imaging system according to the invention.
Figure 2:
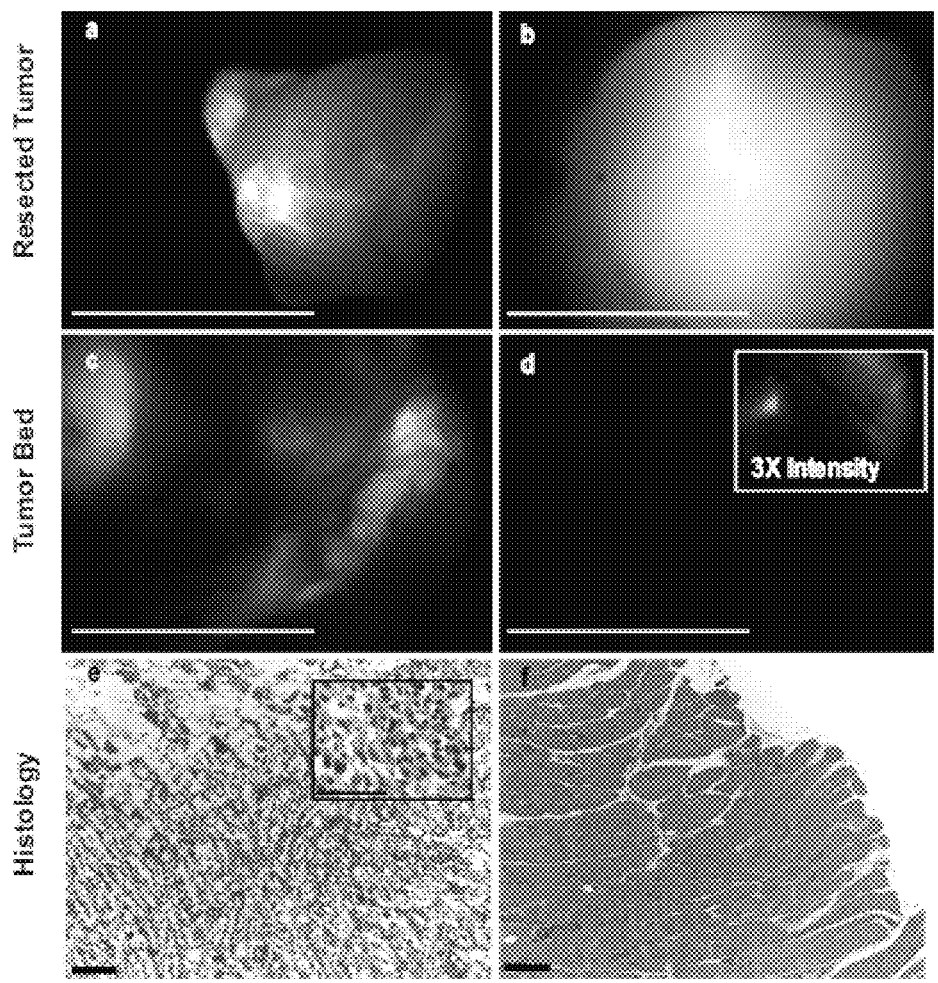
FIG. 2 is a series of photographs showing tumor cell imaging 24 hours after iv injection of Prosense 680. Sarcomas were removed by a gross total resection and the excised tumors were imaged with the device (A and B). Then, the tumor bed was imaged and residual fluorescence suggested (C) the presence or (D) absence of residual microscopic cancer. The intensity level of the inset in panel D has been increased 3-fold for visual reference. Hematoxylin and eosin staining of a biopsy of the tumor beds from C and D confirmed the (E) presence and (F) absence of residual sarcoma cells in the tumor bed, respectively. Inset in (E) shows sarcoma cells at 100× magnification. Scale bars: 5 mm for A-D; 100 μm for E-F; 50 μm for inset in E.

There are over one million cancer surgeries per year performed in the United States and nearly 40% of them miss resecting the entire tumor according to the National Cancer Institute Surveillance Epidemiology and End Results report. For example in breast cancer lumpectomies, positive margins and secondary surgeries occur more than 50% of the time. Failure to remove cancer cells during primary surgery is a leading risk factor for local tumor recurrence and subsequent reoperation. This greatly reduces survival rates and increases the likelihood of tumor recurrence at the primary tumor site as well as metastases.

Moreover, final histopathology of the resected tumor misses 25% of the residual cancer left in the tumor bed, which must be addressed with adjuvant medical therapy (e.g. radiotherapy or chemotherapy). This poor performance of pathology is primarily due to a sampling error since the entire tumor is not stained and imaged.

In a typical solid tumor cancer resection, the surgeon removes the bulk of the tumor and sends it to pathology. The pathologist will then sample the bulk tumor in a few locations and image a stained section under microscope to determine if the surgeon has completely removed all of cancer cells from the patient. Should the pathologist find a portion of the stained sample without normal cells bordering the cancerous cells (a diagnostic known in the medical realm as "positive margin"), the surgeon may be instructed to resect more tissue. However this pathology exercise is a time intensive procedure and often takes days for final results to be sent to the physician. Should a pathology report requiring additional resection return after the patient has completed the initial surgery, this may require the surgeon to perform a second surgery. The current pathology process is not favored for a number of reasons. First, the pathology process relies on sampling a given tumor at certain intervals which may result in missing a critical portion of the tumor and is therefore not a very reliable source of information. In addition, the process disrupts the surgical workflow since the physician and the patient have to wait for the pathology report to return prior to finishing the surgery or return for a second surgery should the pathology process exceed the time window for the first surgery. Leftover cancerous cells in a patient could result in cancer recurrence or additional necessary therapy (e.g. radiation, chemotherapy, etc.). Certainly a system needs to be developed to improve upon the inefficiencies of the pathology process, reducing second surgeries, cancer recurrence, and additional medical therapy for cancer patients.

The present invention addresses the foregoing problems by providing a system and method for precisely isolating a target lesion, resulting in a high likelihood of pathology "clean" margins. This advantageously will often result in the ability to treat a malignant lesion with only a single surgical procedure, with no follow-up surgical procedure required. In particular, the invention provides methods that can thoroughly examine the tumor bed for microscopic residual disease in real-time leading to reducing local recurrence rates and the elimination of secondary surgeries and adjuvant radiation. In addition the invention provides methods that can thoroughly examine the tumor resection in real-time for microscopic residual disease in the margins indicating the need to resect additional tissue. This can also reduce local recurrence and eliminate the need for secondary surgeries and adjuvant radiation.

It has surprisingly been discovered that tissues can be assessed specifically for the detection of cancer cells during surgical excisions using intra-operative optical imaging. Preferably, the sensitivity for the detection allows for single cell detection. In the present invention, methods are presented that allow the assessment of cancer cells during surgical excision. In particular the methods of the invention allow cancer cells to be distinguished from normal cells allowing for complete resection of the tumor, leaving no residual cancer cells in the tumor bed.

In one aspect of the invention, the methods allow for real time detection of residual cancer cells in the tumor bed during surgical resection. In another aspect of the invention, the methods allow real time examination of the resected tumor to insure clean margins. By "clean margin," it is meant that there is an edge of normal tissue surrounding the excised tumor tissue.

The invention also includes details of the probe design. The fluorescent probe is optimized for surface tissue imaging using wavelengths in the visible spectrum. Quiescent in its nominal configuration, the fluorescent probe becomes activated by the diseased tissue. It is composed of a backbone, one or more fluorochromes, one or more quenchers, and one or more pharmacokinetic modifiers.

Cancer detection can include the detection of solid cancers and precancers. Cancer detection can also include differentiating tumor from normal tissue. Any solid cancer can be detected by the methods of the invention. For example, cancers of the digestive system organs, including esophageal cancers, colorectal cancers, and the like; skin; reproductive organs, such as prostate, ovarian, uterine and cervical cancers, breast cancer; brain cancer; cancers of the lymphatic system and bone; and the like.

More specifically, the present invention provides methods and systems to identify and spatially localize abnormal tissues and cells using optical techniques. These methods and systems are thus useful for the treatment of many types of diseases and conditions characterized by abnormal tissue or cells and are particularly useful as surigal or semi-invasive techniques for screening areas of interest to identify and spatially locate abnormalities. Abnormal tissues and cells include for example cancerous tissue or other pathological abnormality.

The imaging method and system of the present invention can be described as follows. Although this example is for abnormal cells detected for solid tumor cancer patients, it is understood that this flow could be adapted to other disease areas.

The probe is administered to the subject which subsequently travels to the cancerous tumor site.

The tumor site activates the "fluorochrome", "fluorochrome-fluorochrome" or "fluorochrome-quencher" probe, enabling the fluorochrome(s) on the probe to be excited with electromagnetic radiation (light).

The surgeon resects the tumor or exposes the cancerous site. The imaging device with single cell resolution then excites the activated probes and identifies areas at or near the exposed surface with remaining cancerous cells.

The surgeon can then biopsy or remove the remaining cancerous cells, based on the guidance of the imaging system to prevent cancer recurrence, additional surgery, or other medically necessary treatments.

Although there exists an immediate need for abnormal tumor cell detection for cancer surgeries, it can be further postulated that such a system would be beneficial for other types of operations as well. Using different activatable or target probes, one could image abnormal cells via endoscopy, via imaging catheters, or via open surgical bed imaging in various central nervous system disorders (e.g. Parkinson's disease), various cardiovascular system disorders (e.g. ischemia), or various orthopedic disorders (e.g. osteoporosis). It should be understood that the above disease areas are not limiting and that other abnormal cells could be detected.

According to one embodiment, optical detection techniques are used in conjunction with the administration of a molecular imaging probe for diagnostic purposes to screen an area of interest to identify properties of the tissues and cells to locate abnormalities with a high degree of spatial resolution. Optical detection techniques may be used for examining an area of interest that is directly exposed to an energy source(s) (e.g., laser, infrared, radiation, etc) and detector(s), such as an area of interest exposed during a surgical procedure, or an area of interest exposed to an invasive or semi-invasive instrument, such as a laproscope, endoscope, probe, fiber optic cables, or the like.

Additionally, methods and systems of the present invention may be interfaced with stereotaxic systems to assist medical personnel in spatially identifying tissues and cells during surgery and locating areas of abnormalities, both during surgery, and during recovery.

Yet another application for methods and systems of the present invention involves in situ monitoring an area of interest to evaluate the progression, or recession, of an abnormality in an area of interest, and to monitor, in situ, the effect of a treatment regimen or agent on an identified or suspected abnormality.

For some applications where the area of interest is directly exposed, topical application of the molecular imaging probes may be preferred to other types of delivery systems. Thus, for example, topical application of a molecular imaging probe, to an area of interest such as a tissue, tumor bed, resected tumor, or to a surface of an internal organ is followed by acquisition of one or more data sets indicative of one or more optical properties of the area of interest. Comparison of data points within the data set acquired following application of the molecular imaging probes highlights areas of enhanced optical change indicative of a characteristic and thereby highlights the location of abnormal tissue. Comparison of data set(s) acquired following administration of the molecular imaging probe to control data indicative of one or more optical properties of normal tissue of the same type, or to control data acquired at the area of interest prior to application of the molecular imaging probe, provides identification and spatial localization of abnormal tissue, particularly cancerous tissue, by highlighting the different optical properties of the tissue following administration of the molecular imaging probe.

In one embodiment, a molecular imaging probe is administered to provide perfusion of the area of interest. Initial detection of the molecular imaging probe is manifest in many types of cancer tissue first, because cancer tissue is differently vascularized compared to non-cancerous tissue and many molecular imaging probes therefore perfuse more rapidly into cancerous tissue than normal tissue. Solid tumor margins are generally the first morphological indications of cancer tissue detected by comparison of a control or background data set with a data set acquired from an area of interest containing cancerous tissue following administration of a molecular imaging probe. In applications in which comparison data is output as an image and the detector is, for example, a camera, a comparison image shows darkened lines outlining a solid tumor mass.

Methods and systems of the present invention may also be used to assist in the selection of tissue samples for biopsy. The selection of the biopsy sample is critical—every effort should be made to enhance the likelihood of including abnormal tissue. Yet, tissue biopsies are invasive and may affect important tissues, and therefore should be limited to reduce trauma and preserve function of the tissue. Lymph nodes are frequently biopsied, for example, in an effort to evaluate the extent and progression of various cancers.

Administration of a molecular imaging probe followed by illumination and optical detection to identify and spatially localize areas of abnormal tissue greatly aids in the selection of tissue samples to biopsy. Specifically, with the aid of an optical contrast enhancing agent and the optical techniques of the present invention, the likelihood of obtaining a biopsy sample including abnormal tissue is substantially increased. Optical source(s) and detector(s) may be incorporated in an invasive or non-invasive biopsy instrument, and the contrast enhancing agent may be administered in situ or in another fashion that provides application of the contrast enhancing agent in the area of interest.

Yet another application for methods and systems of the present invention involves in situ monitoring an area of interest to evaluate the progression, or recession, of a condition involving abnormal characteristics such as pathological or tumor tissue, in an area of interest, and to monitor, in situ, the effect of a treatment regimen or agent on an identified or suspected area of interest, such as a tumor. Methods and systems of the present invention may be employed, for example, to provide frequent screening or monitoring of cancerous tissue to rapidly detect any progression that would benefit from additional or different treatment agents or regimen.

Diagnostic and monitoring procedures, optionally, involve administration of a molecular imaging probe to an area of interest, followed by illumination and detection of one or more optical properties of the area of interest. A data set may be examined to identify areas of differential optical properties that may be indicative of normal or abnormal tissue. Comparison of data set(s) representing one or more optical properties of spatially defined locations in the area of interest following administration of the molecular imaging probe may be made as described above. Such comparisons are preferably made continuously or at predetermined intervals following administration of the contrast enhancing agent to provide information relating to the time course of differential optical properties enhanced by the contrast enhancing agent at the area of interest.

The interaction between the energy source (e.g. emr source) and the molecular imaging probe depends upon the specific agent being used. For example, in the case of a fluorescent dye, the preferred wavelength of emr is one which excites the dye, thereby causing fluorescence. However, for many contrast enhancing agents, such as indocyanine green, the preferred wavelength of emr is one which is absorbed by the dye.

The inventive methods and systems are superior to established tumor detection and localization techniques, such as MRI, because they are capable of distinguishing single cancer cells that generally are not distinguishable using alternative techniques. Another advantage over traditional tumor detection and localization techniques is that the present invention provides for real time analysis of the tumor bed and resected tumor tissue. Additionally, updated comparison data sets may be provided on a continuous or frequent basis during a surgical procedure, for example, by readministering a stimulus or a molecular imaging probe. A stimulus or molecular imaging probe may be administered on multiple occasions during a surgical procedure, for example, to examine an area of interest for functional or dysfunctional tissue, or for residual tumor tissue/cells. Methods and systems of the present invention may be implemented using readily available equipment.

The molecular imaging probe may be any agent that provides differential contrast enhancement between normal and abnormal tissue. Emr-absorbing and fluorescent agents are suitable. During surgical resection of a solid tumor, it is important that the agent be activated in the tumor area for imaging either less than about 2 hours from administration or between about 12 and 36 hours post administration.

Yet another aspect of the inventive method and systems involves using an emr absorbing or fluorescent dye conjugated to a targeting molecule, such as an antibody, hormone, receptor, or the like. According to one embodiment, the targeting molecule is a monoclonal antibody or fragment thereof specific for surface marker of a tumor cell or a cell that circulates in the blood stream. For example the targeting moiety is HERCEPTIN®, RITUXAN®, MYLOTARG® (gemtuzumab ozogamicin), BEXXAR® (tositumomab), or ZEVALIN® (britumomab tiuxetan)

When fluorescent agents are used, the area of interest is illuminated with emr containing excitation wavelengths of the fluorescent agent, but not emission wavelengths. This can be accomplished by use of a cutoff filter over the emr source. Preferably, the optical detector is coupled to an image intensifier or micro channel plate (e.g., KS-1381 Video Scope International, Wash D.C.) to increase the sensitivity of the system by several orders of magnitude and allow for visualization of cells having fluorescent dyes attached thereto.

Molecular Imaging Probes

As used herein, "probe" means an identifiable molecule which is used to detect the presences of other molecules.

As used herein, "fluorochrome" means a molecule which becomes fluorescent by absorbing energy (light) at one or more specific wavelengths by exciting ground-state electrons into a higher energy level and then emitting energy (light) at one or more slightly different wavelengths when the excited electrons return to the ground-state energy level.

As used herein, "dark quencher" means a molecule which absorbs light radiation at one or more specific wavelengths and dissipates the energy absorbed in the form of heat; thus, a dark quencher does not emit fluorescent light.

As used herein, "pharmacokinetic modifier" means a molecule which is attached to the molecular imaging probe which inhibits undesired biodegradation, clearance, or immunogenicity of the probe.

As used herein, "spacer" means a molecule which is attached to the molecular imaging probe which results in further separating the components or which is intended to provide a convenient mechanism for connecting two components together.

In general, the molecular imaging probes include one or more imaging moieties (e.g., optical imaging). Optionally, the molecular imaging probes include one or more targeting moieties. In some embodiments, the probes include an imaging moiety and a targeting moiety which can be linked to one another, for example, by one or more covalent bonds, by one or more covalent associations, or any combination thereof.

The imaging moiety can be any moiety that interacts with light (e.g., a moiety that can emit detectable energy after excitation with light) and can include optically detectable agents, optically detectable dyes, optically detectable contrast agents, and/or optical dyes.

Most available fluorescent probes for clinical or pre-clinical use image through thick sections of tissue as the imaging modality is typically located outside of the body and the probe is located deep within the tissue. This necessitates the use of near infrared light wavelengths, and associated near infrared fluorochromes, which are capable of penetrating deep tissue. At times, the tissue of interest is exposed during open surgery and detection from deep tissue needs to be avoided in order to assess the condition of only the exposed surface. Therefore, a system which preferentially images cells at or near the surface of the tissue of interest would be beneficial in a clinical or pre-clinical setting to examine an open wound. In this case, systems using wavelengths in the visible light or "far red" spectrum are suitable for detecting abnormal cells close to the surface of the tissue while ignoring deep tissue emissions. Although there is no common definition for the cut-off between visible wavelengths and near infrared wavelengths, it is generally accepted to be around 700 nm. The International Commission on Illumination (CIE) recommends 700 nm as the cut-off between visible light and the first NIR band (IR-A) whereas the ISO 20473:2007 standard designates that near infrared does not start until 780 nm.

Imaging moieties in the visible light spectrum of 350-670 nm are preferred to selectively view cells at or near the surface (within about 1 cm from the surface, preferably 1 mm, 2 mm, 3 mm, 4 mm, 5 mm, 6 mm, 7 mm, 8 mm, 9 mm or less) and exclude deep tissue emission. Near infrared wavelengths are not needed in this application since deep tissue penetration of the energy is not desired. Tissue absorbance and autofluorescence is high between 400 nm and 500 nm while slowly dropping off around 570 nm. Thus, the longer wavelengths in the visible spectrum are preferred for use in the methods according to the invention. Examples of fluorochromes in the visible light spectrum which could be used include but are not limited to: Cy3, Cy3.5, Cy5, Alexa 568, Alexa 546, Alexa 610, Alexa 647, ROX, TAMRA, Bodipy 576, Bodipy 581, Bodipy TR, Bodipy 630, VivoTag 645, and Texas Red. Other fluorochromes in the visible light spectrum are know to those skilled in the art and are useful in the methods of the invention.

Enzyme activatable probes typically suppress any fluorescence until activated by an enzyme. The probes are constructed of one or more fluorochromes which emit light when excited by light at a different frequency. There are numerous types of enzyme activatable probes. For example, Weissleder et al. in U.S. Pat. No. 6,592,847 describes "self-quenched" probes which contain at least two fluorochromes which are spaced close enough together such that the fluorochromes quench each other when they encounter their excitation light. Upon cleavage of the probe by enzyme activity, the fluorochromes are separated and detectable by their emission of light. There are also "non self-quenched" probes which include one fluorochrome and one dark quencher. In this case, the dark quencher, which never emits light, prohibits emission light from the fluorochrome until the probe is cleaved and the fluorochrome and dark quencher are separated.

Preferably, the molecular imaging probe includes an activatable probe. By activatable imaging probe it is meant a molecule that exhibits no fluorescence emission or its fluorescence emission is quenched in its nominal configuration, but its fluorescence emission is released upon enzymatic cleavage of its backbone. Activatable imaging probes have been specifically designed to target enzyme families with well established catalytic mechanisms including proteases, kinases, lipases, glycosylases, histone deacylases, and phosphatases. Optimally, the activatable imaging probe targets an enzyme that is either preferentially expressed in cancer cells or is up-regulated in cancer cells. Thus, the imaging moiety is only active in cancer cells, allowing for discrimination between cancer and normal tissue. For example, the probe targets an enzyme in the cysteine protease family (e.g., caspase), cysteine cathepsin family (e.g. cathepsin B), serine protease family or the aspartic protease family.

In one embodiment of this invention, the activatable imaging probe is preferentially designed to be non-enabled fluorescently until activated by enzymatic activity in the diseased tissue. In one case, one fluorochrome is designed into the probe at a location close to another fluorochrome such that the fluorochromes quench each other. In another case, one fluorochrome is designed into the probe at a location close to a dark quencher such that the probe is not enabled until activated by an enzyme. A dark quencher emits no fluorescence, but absorbs fluorescence from nearby fluorochromes. Suitable dark quenchers include but are not limited to: QSY (diarylrhodamine derivatives) type quenchers (e.g. QSY21, QSY7, QSY9, QSY35), dabcyl type quenchers, Iowa black FQ and RQ quenchers, and Black Hole quenchers.

In some embodiments, the optical imaging moiety can be a fluorescent moiety (e.g., a fluorochrome). In other embodiments, the optical imaging moiety can be a phosphorescent moiety.

Additional various fluorochromes are described in the art and can be used to construct molecular imaging probles according to this invention. These fluorochromes include but are not limited to cyanine, hemi-cyanine, azacarbocyanine, sulfo-benze-indocyanine, squarain, benzopyrylium-polymethine, and 2- or 4-chromenyliden based merocyanine dyes.

Fluorochromes that can be used to construct molecular probes are also described in U.S. Pat. Application No. 2002/0064794, U.S. Pat. Application No. 20050214221, U.S. Pat. Application No. 2005/0171434, PCT Publication No. WO 02/24815, U.S. Pat. Nos. 5,800,995, 6,027,709, PCT Publication No. WO 00/53678, PCT Publication No. WO 01/90253, EP 1273584, U.S. Patent Application No. 2002/0115862, EP 1065250, EP1211294, EP 1223197, PCT Publication No. WO 97/13810, U.S. Pat. Nos. 6,136,612, 5,268, 486, 5,569,587, 6,737,247, 7,383,076 and Lin et al., 2002 *Bioconj. Chem.* 13:605-610, the entire teachings of which are incorporated herein by reference.

In some embodiments, the imaging moiety can be porphrin, quantum dot, fluorescein, rhodamine, tetramethylrhodamine, eosin, erythrosin, coumarin, methylcoumarins, pyrene, Malacite green, stilbene, Lucifer Yellow, Cascade Bleum, or Texas Red. Other optical imaging moieties can be selected as desired, for example, from Molecular imaging probes.

Other suitable molecular imaging probes include for example TOPRO (to stain dead cells), dyes to detect proliferating cells (for example, BrdU), non-cell permeable dyes to detect apoptotic (e.g. permeable) cells, pH sensing dyes and other DNA intercalators.

One skilled in the art would recognize that any moiety that is capable of emitting detectable signal is suitable for use as a molecular imaging probe.

In addition, the fluorescent imaging probes need to be optimized for either a short term (less than two hours, preferably about 5 minutes, 10, minutes, 15 minutes, 30 minutes, 45 minutes, 1 hour, 1 hour and 15 minutes, 1 hour and 30 minutes, 1 hour 45 minutes, 2 hours or less) or between 12 and 36 hours post-administration activation time in order to be clinically relevant. An imaging probe that is optimally imaged at other times would disrupt the current pre-operative procedures followed by the majority of surgery centers. Subjects are typically brought in one day prior to the surgical procedure for a blood draw and are subsequently brought into the facility well in advance of the surgical procedure time on the day of the surgery necessitating these two specific time windows of operation.

The imaging time window can be adjusted by designing the probe with specific pharmacokinetic modifiers of varying size and type. The pharmacokinetic modifiers can be used to optimize the clearance of the probe from the body so that it quickly reaches the target tissue, does not toxically build up in the kidney or liver, and does not clear from the body too rapidly prior to imaging the target tissue. Note that the method of probe administration also determines the choice of pharmacokinetic modifier. For example, if the probe is administered systemically, the pharmacokinetic modifier should be designed such that the probe has ample time to reach the target tissue via the body's vascular supply. Should the probe be administered topically to an open in-vivo tissue bed, the pharmacokinetic modifier should be designed such that the probe has time to diffuse into the tissue via osmotic pressure differentials, or other bio-transport mediated methods. Furthermore, should the probe be administered topically to an ex-vivo tissue resection, the probe needs to be optimized to diffuse into the tissue at a set, predictable diffusion rate such that imaging of surface tissue can be performed.

In some embodiments, the molecular imaging probe includes pharmacokinetic modifiers of adjustable molecular weight and size which allows the bio-distribution and diffusion rate of the molecular imaging agent to be controlled. For example, polyethylene glycol (PEG) and/or dextran can be used as a pharmacokinetic modifier because its chain length, and thus molecular weight, can be precisely controlled and readily conjugated to the imaging probe. Other forms of PEG that can be used are polyethylene oxide (PEO) or polyoxyethylene (POE). Other suitable pharmacokinetic modifiers are methoxypolyethylene glycol (MPEG), methoxypolypropylene glycol, polyethylene glycol-diacid, polyethylene glycol monoamine, MPEG monoamine, MPEG hydrazide, MPEG imidazole, copolymers of polyethylene glycol and monoxypolypropylene glycol, branched polypropylene glycol, polypropylene glycol, and polylacic-polyglycolic acid. Optionally, any fatty acid, lipid, phospholipid, carbohydrate, sulfonate, polysulfonate, amino acid, or peptide can be used as a pharmacokinetic modifier to tune the biodistribution of the molecular imaging probe.

Importantly, the size and weight of pharmacokinetic modifiers can be adjusted to modify the kinetics of the probe. Smaller sizes and weights are more useful for topical applications where the probe is directly applied to target tissue and immediate imaging is necessary. Larger sizes and weights allow for the probe to be injected and travel to the target tissue via vascular routes. Further small modifications of the size and weight can be used to adjust the retention time of the probe in the target tissue. The molecular probe needs to reside in the target tissue at least about an 1 hour and up to about 48 hours. If the retention time is less than 1 hour, the imaging procedure will not be readily adopted from a commercial standpoint. Retention times exceeding 48 hours are unnecessary from a commercial standpoint.

The pharmacokinetic modifiers need to be optimized to allow imaging within about 2 hours of administration or between about 12 and 36 hours post probe administration. In some embodiments of the present invention, probes with PEG attachments around 2,000 g/mol and between 20,000 g/mol and 40,000 g/mol are preferably used to target topical applications (small molecular weight PEG) and injectable (larger molecular weight PEG) versions of the molecular imaging probe. Although these are examples, other PEG sizes and different pharmacokinetic modiefiers can be used. PEG molecules are typically available in a large array of molecular weights from 300 g/mol to 10,000,000 g/mol.

Preferably, the pharmacokinetic modifier is between 500 g/mol and 100,000 g/mol.

In some embodiments, the molecular imaging probe has a binding moiety that targets serum albumin. Once bound, the albumin will transport the imaging probe through the circulatory system enventually reaching the tumor site.

In some embodiments, the molecular imaging probe can further include a polymeric backbone. Probe polymeric backbone design will depend on considerations such as biocompatibility (e.g., toxicity and immunogenicity), diffusion rate, serum half-life, useful functional groups (e.g., for conjugating imaging moieties and target moieties), and cost. Useful types of polymeric backbones include polypeptides (polyamino acids), polyethyleneamines, polysaccharides, aminated polysaccharides, aminated oligosaccharides, polyamidoamines, polyacrylic acids, and polyalcohols.

In some embodiments the backbone includes a polypeptide formed from L amino acids, D-amino acids, G-amino acids, R-amino acids, K-amino acids or a combination thereof. Such a polypeptide can be, e.g., a polypeptide identical or similar to a naturally occurring protein such as albumin, a homopolymer such as polylysine, or a copolymer such as a D-tyr-D-lys copolymer. When the polymeric backbone is a polypeptide, the molecular weight of the probe can be from about 2 kiloDaltons (kD) to about 1000 kD. A polymeric backbone can be chosen or designed so as to have a suitably long in vivo persistence (e.g., half-life) inherently. In some embodiments, a rapidly biodegradable polymeric backbone such as polylysine can be used in combination with covalently-linked pharmacokinetic modifier. Examples of other useful pharmacokinetic modifiers include polysaccharide, polyamidoamine, polyethyleneamine or polynucleotide. Synthetic, biocompatible polymers are discussed generally in Holland et al., 1992, "Biodegradable Polymers," Advances in Pharmaceutical Sciences, 6:101-164.

In some embodiments, the imaging moiety and the targeting moiety can each be attached to the same or different atoms of a polymeric backbone (e.g., by one or more covalent bonds and/or one or more covalent associations). In other embodiments, the imaging moiety and the targeting moiety can be linked to one another as described elsewhere and then attached to the polymeric backbone through either the imaging moiety or the targeting moiety.

Various fluorochromes, polymeric backbones, protective side chains, and targeting moieties are also described in, for example, Weissleder et al., U.S. Pat. No. 6,083,486, which is hereby incorporated by reference.

Figure 19:
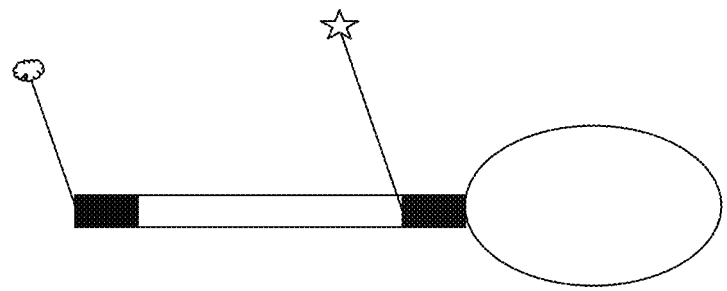
FIG. 19 is a schematic of one probe design with the fluorochrome located near the pharmacokinetic modifier.
Figure 20:
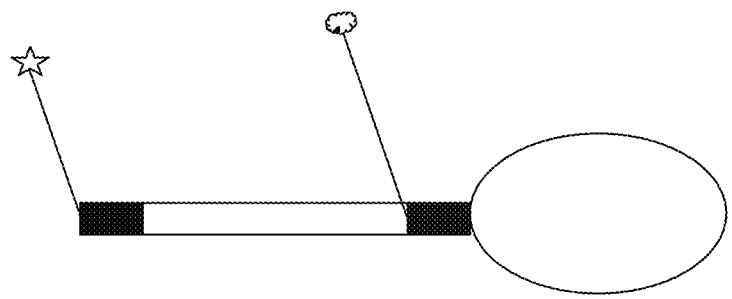
FIG. 20 is a schematic of one probe design with the quencher located near the pharmacokinetic modifier.
Figure 21:
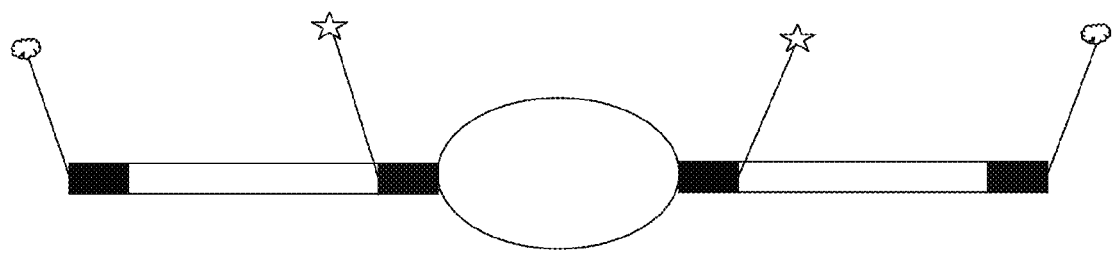
FIG. 21 is a schematic of one probe design with two fluorochromes and two quenchers.
Figure 22:
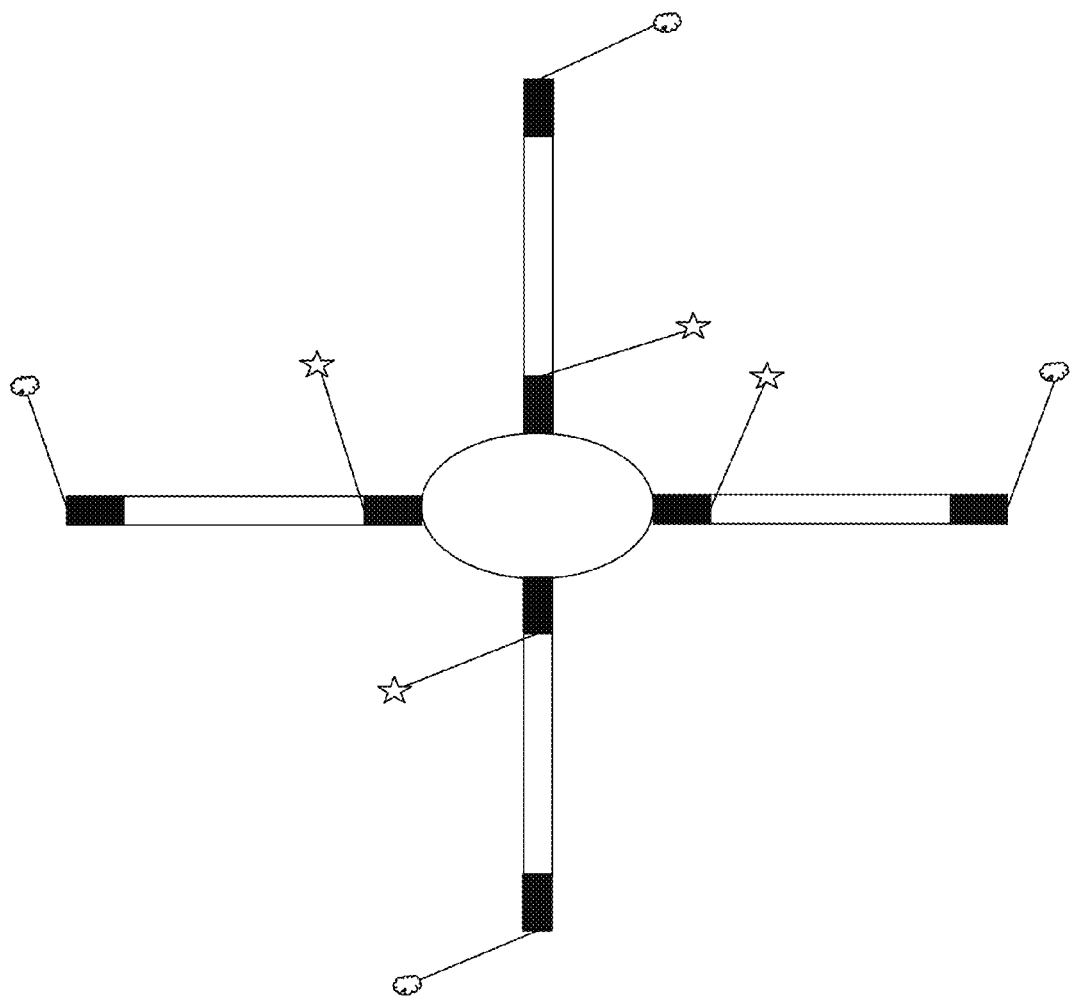
FIG. 22 is a schematic of one probe design with four fluorochromes and four quenchers.
Figure 23:
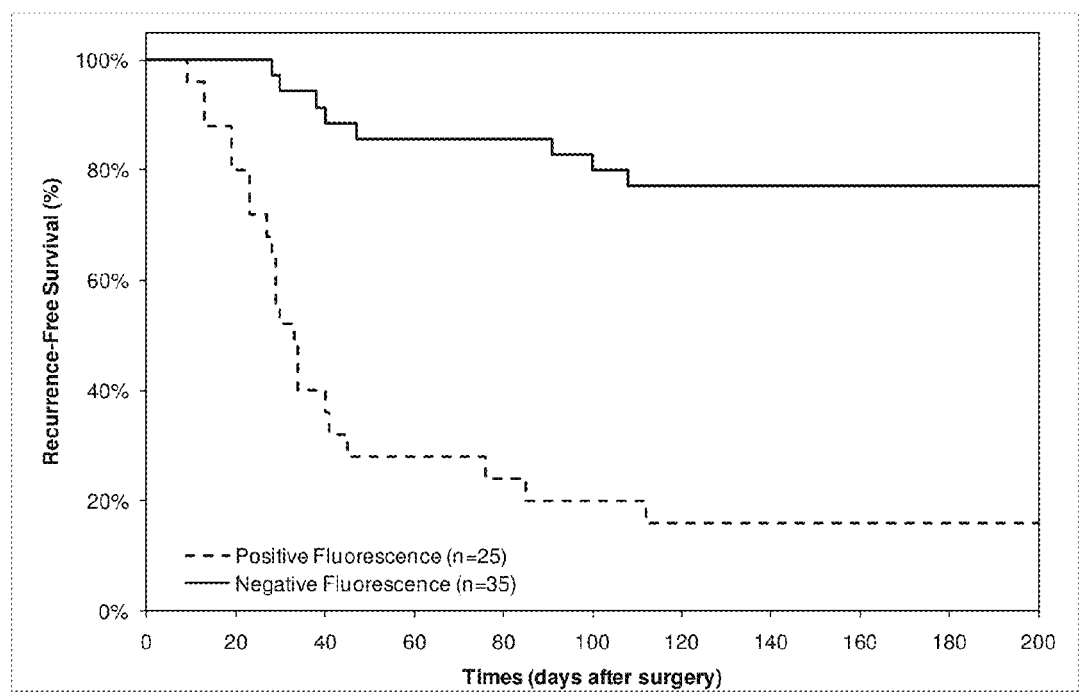
FIG. 23 is a Kaplan-Meier curve for relapse-free survival of a mouse sarcoma model using intra-operative imaging classification of the tumor bed.

FIG. 19 shows a schematic of one type of imaging probe. The oval represents the pharmacokinetic modifier, the star represents a fluorochrome, the black box represents a spacer, the white box represents the backbone, and the cloud represents the quencher. Note that the schematic is just one representation of such a probe, and additional components of the same type can be added, subtracted, and re-oriented as noted in this invention. For example, the fluorochrome and quencher can swap places, the spacers can be removed, and additional quenchers, fluorochromes, backbones, and pharmacokinetic modifiers can be added as shown in FIGS. 20-22.

Spacers are used to connect the various components and provide optimal distances between fluorochrome(s) and quencher(s). The spacers allow the enzymes of the diseased tissue room to cleave the polypeptide backbone. If the molecular probe is too dense, the enzymes will be less likely to access the right location of the probe and properly activate the drug. Spacers are typically PEG2, PEG2 attached to an amino acid; 6-carbon chain (aminohexanoic acid, Ahx); an amino acid sequence SRK; an amino acid D; or an amino acid C. Activation sites for abnormal cells can occur in the backbone or in the side chains of the fluorochrome(s) or quencher (s).

In one embodiment, the molecular probe can be defined according to the following formula: $[S1]_i\text{-P-}[([S2]_j\text{-F})\text{-A-}([S3]_k\text{-Q})\text{-}[S4]_m]_n$ where S1, S2, S3, and S4 are spacers; i is 0 or 1; P is a pharmacokinetic modifier; F is a fluorochrome; A is an amino acid sequence; Q is a dark quencher; j is 0 or 1; k is 0 or 1; m is 0 or 1; and n is 1, 2, or 4.

In another embodiment of the present invention, the molecular imaging probe has the following formula: $\text{P-}([S1]_j\text{-Q})\text{-A-}([S2]_k\text{-F})$ where S1 and S2 are spacers; P is a pharmacokinetic modifier; F is a fluorochrome; Q is a dark quencher; A is an amino acid sequence; j is 0 or 1; k is 0 or 1.

The present invention includes examples of preferred chemical structures for the molecular probe. One such formula is PEG-SRK(Cy5)-GGRK(QSY21)-D where the PEG is size 2,000 g/mol. Another formula is C(PEG)-SRK(Cy5)-GGRK(QSY21)-D where the PEG is size 20,000 g/mol. Another formula is [QSY21-Ahx-GGRK(Cy5)-PEG2-C]$_n$-PEG, wherein n=1, 2, or 4 and the PEG is size 20,000 g/mol or 40,000 g/mol. Another formula is Cy5-Ahx-GGRK(QSY21)-PEG2-C(PEG) where the PEG is size 20,000 g/mol. Another formula is QSY21-LRGGRK(Cy5)-PEG2-C(PEG) where the PEG is size 20,000 g/mol.

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| α-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienylalanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| ρ-Aminophenylalanine | | Phe(pNH$_2$) |
| N-methylvaline | | MeVal |
| Homocysteine | | hCys |
| Homoserine | | hSer |
| ε-Amino hexanoic acid | | Aha |
| δ-valeric acid | | Ava |
| 2,3-Diaminobutyric acid | | Dab |

In some embodiments, the molecular imaging probes can have a relatively long half-life in the blood pool, e.g., having a half-life in the blood pool of at least about 2 hours (e.g., at least about 6 hours, at least about 12 hours, at least about 20 hours, at least about 30 hours, at least about 40 hours, or at least about one week).

The molecular imaging probe (e.g., optical imaging probe) accumulates in diseased tissue at a different rate than in normal tissue. For example, the rate of accumulation of the agent can be at least 5%, 10%, 20%, 30%, 50%, 75%, or 90% faster in diseased tissue compared to normal tissue. Alternatively, the rate of accumulation of the agent can be at least 5%, 10%, 20%, 30%, 50%, 75%, or 90% slower in diseased tissue compared to normal tissue Alternatively, the molecular probe is metabolized in diseased tissue at a different rate than in normal tissue. For example, metabolism of the imaging agent can occur at a rate that is at least 5%, 10%, 20%, 30%, 50%, 75%, or 90% faster in diseased tissue compared to normal tissue. For example, metabolism of the imaging agent can occur at a rate that is at least 5%, 10%, 20%, 30%, 50%, 75%, or 90% slower in diseased tissue compared to normal tissue.

Optionally, the imaging agent becomes trapped in cells.

In another embodiment the diseased tissue is cancerous and the imaging agent accumulates in malignant tissue at a different rate than in normal or benign tissue.

One preferred embodiment of the invention is based upon the well-accepted observation that malignant tissue may be easily distinguished from benign or normal tissue by its increased rate of glucose metabolism. Specifically, rapidly dividing cells have been shown to exhibit enhanced glucose metabolism, a requirement necessary to sustain their increased need for ATP generation and substrate storage. In addition to normal physiologically-related growth processes, cancer cell growth is heavily dependent upon increased glucose metabolism. Furthermore, the correlation between increased glucose metabolism and tumor growth has been well documented and exploited in the development of drugs aimed at blocking glucose metabolism for therapeutic purposes. Glucose transport across cell membranes requires the presence of specific integral membrane transport proteins, which includes the facilitative glucose carriers. Since the initial identification of the human erythrocyte glucose transporter, GLUT-1, more than 12 additional family members have been described and several have been shown to be overexpressed in various human cancers and cancer cell lines, leading to speculation that aberrant regulation of glucose metabolism and uptake by one or more transporter subtypes may correlate with tumor genesis.

For imaging of glucose metabolism, a molecular imaging probe should be able to readily permeate the cell membrane and enter the cytosol. The optical metabolite imaging probe should also preferably be capable of interacting with specific enzymes involved in glucose metabolism. Many enzymes, receptors, and transporters are quite permissible. For example, GLUT-2, which normally helps transport glucose across the cell membrane, also recognizes and transports [$^{19}$F]-deoxyglucose (FDG) and $^{99m}$Tc-chelate-deoxyglucose. In addition, hexokinase, which is an enzyme that catalyzes the first step in glucose metabolism, (i.e., the phosphorylation of glucose to glucose-6-phosphate) is also quite permissible and can carry out this chemical reaction on FDG and $^{99m}$Tc-chelate-deoxyglucose. Therefore, a preferred embodiment of the present invention for imaging glucose metabolism is comprised of 1-30 glucose or deoxyglucose molecules chemically linked to a suitable fluorochrome. Ideally, the molecular probe would become trapped in the cell. A molecular imaging probe could be used to diagnose and stage tumors, myocardial infarctions and neurological disease. In another embodiment, the metabolically recognizable molecule is not a sugar. In a preferred embodiment, 2 or 3 or more glucose or deoxyglucose molecules are chemically linked to a suitable fluorochrome.

Another preferred embodiment is based on the well-accepted observation that malignant tissue has a higher rate of cellular proliferation when compared to benign or normal tissue. The rate of cellular proliferation can be measured by determining the rate of DNA synthesis of cells, which can be measured using nucleotide based metabolites such as thymidine. Thus, a preferred embodiment of the present invention for imaging cellular proliferation is comprised of 1-30 thymidine molecules, and analogs thereof, chemically linked to a suitable fluorochrome. In a preferred embodiment, 2 or 3 or more thymidine molecules are chemically linked to a suitable fluorochrome.

In another embodiment, the diseased tissue is in the central nervous system and the imaging agent is metabolized or accumulates in the diseased tissue at a different rate when compared to normal tissue. One preferred embodiment of the invention is based upon the well-accepted observation that the density of dopamine transporters and level of dopamine metabolism in the central nervous system is elevated or decreased in a number of different disease states including Parkinson's disease, Tourette's Syndrome, Lesch-Nyhan Syndrome, Rhett's Syndrome, and in substance abusers. Proper dopamine metabolism also is required to maintain a state of psychological well-being.

For imaging of increased or decreased levels of dopamine transporters and level of dopamine metabolism, an optical metabolite imaging probe should be able to readily bind to the dopamine transporter (DAT) and, ideally, enter the cytosol of the cell. The dopamine transporter is known to bind to and transport a wide range of metabolites including L-dopa and tropanes. Therefore, these metabolites could be used to image increased or decreased levels of dopamine transporters and dopamine metabolism. Thus, a preferred embodiment of the present invention for imaging increased or decreased levels of dopamine transporters and level of dopamine metabolism, is comprised of 1-30 L-dopa, dopamine, tropane or raclopride molecules, or combinations thereof, chemically linked to a suitable fluorochrome. In addition, preferred brain imaging agents of the present invention also have blood brain barrier permeability. In a preferred embodiment, 2 or 3 or more L-dopa, dopamine, tropane or raclopride molecules, or combinations thereof are chemically linked to a suitable fluorochrome.

In another embodiment, the diseased tissue is in the cardiovascular system and the imaging agent is metabolized or accumulates in the diseased tissue at a different rate when compared to normal tissue. One preferred embodiment of the invention is based upon the well-accepted observation that many common cardiac disorders are the result of imbalances of myocardial metabolism. Oxidation of long chain fatty-acids is the major energy pathway in myocardial tissue and abnormal rates of cellular uptake, synthesis and breakdown of long-chain fatty acids are indicative of various cardiac diseases including coronary artery disease, myocardial infarction, cardiomyopathies, and ischemia (Railton et al., 1987 *Euro. J NucL. Med.* 13:63-67; and Van Eenige et al., 1990 *Eur. Heart J.* 11:258-268).

For imaging of increased or decreased levels of cellular uptake, synthesis and breakdown of long-chain fatty acids in vascular disease, an optical metabolite imaging probe should be able to permeate the cell membrane and enter the cytosol and, preferably, interact with enzymes involved in long-chain fatty acid metabolism. Fatty acids generally enter cells via passive diffusion. After cellular entry, many fatty acids undergo β-oxidation, which is catalyzed by coenzyme A synthetase. Therefore, a preferred embodiment of the present invention for imaging cardiovascular disease is comprised of 1-30 fatty acid molecules chemically linked to a suitable fluorochrome. In a preferred embodiment, 2 or 3 or more fatty acid molecules are chemically linked to a suitable fluorochrome.

Another preferred embodiment of the invention is based upon the well-accepted observation that imbalances in osteoblast activity is indicative of several disease states including osteoporosis, osteoblastic cancer metastases, early calcification in atherosclerosis and cancer lesions, arthritis and otoslcerosis. Phosphonates and analogs thereof localize in areas where osteoblast activity is high, including areas of active bone remodeling (Zaheer et al., 2001, *Nature Biotech* 19:1148-1154). Thus, a preferred embodiment of the present invention for imaging bone diseases and also atherosclerosis and otoslcerosis is comprised of 1-30 methylene diphosphonate, pyrophosphate, and/or alendronate molecules chemically linked to a suitable NIRF. In a preferred embodiment, 2 or 3 or more methylene diphosphonate, pyrophosphate, and/or alendronate molecules are chemically linked to a suitable fluorochrome.

Another preferred embodiment of the invention is based upon the well-accepted observation that tumors and infarcted regions are hypoxic when compared to normal or unaffected tissue. Compounds such as nitroimidizoles, such as misonidazole, are known in the art that preferentially accumulate and are retained in hypoxic areas. In cells with reduced oxygen content, these compounds are metabolized by cellular reductases, such as xanthine oxidase, and subsequently become trapped inside the cell. Therefore, a preferred embodiment of the present invention for imaging hypoxia is comprised of 1-30 misonidazole molecules chemically linked to a suitable fluorochrome structure. In a preferred embodiment, 2 or 3 or more misonidazole molecules are chemically linked to a suitable fluorochrome.

The targeting moiety can be selected on the basis of its ability to maximize the likelihood of probe uptake into host response cells in the pathology or at its periphery and/or into the cells of the pathology itself. The targeting moiety is any compound that directs a compound in which it is present to a desired cellular destination. In some aspects, the cell targeting moiety is capable of being internalized into a cell. The targeting moiety binds specifically to an endocytosing receptor or other internalizing unit on a tumor cell. For example, the targeting moiety is a compound that is not typically endocytosed but is internalized by the process of cross-linking and capping. Thus, the targeting moiety directs the compound across the plasma membrane, e.g., from outside the cell, through the plasma membrane, and into the cytoplasm. Alternatively, or in addition, the targeting moiety can direct the compound to a desired location within the cell, e.g., the nucleus, the ribosome, the endoplasmic reticulum, a lysosome, or a peroxisome. Targeting moietes include for example, polypeptides such as antibodies; viral proteins such as human immunodeficiency virus (HIV) 1 TAT protein or VP22; cell surface ligands; peptides such as peptide hormones; or small molecules such as hormones or folic acid. Optimally, the receptor for the targeting moiety is expressed at a higher concentration on a tumor cell compared to a normal cell. For example, the receptor is expressed at a 2, 3, 4, 5, or more-fold higher concentration on a tumor cell compared to a non-tumor cell.

The term "antibody" as used herein refers to immunoglobulin molecules and immunologically active portions of immunoglobulin molecules, i.e., molecules that contain an antigen binding site that specifically binds (immunoreacts with) an antigen. Such antibodies include, polyclonal, monoclonal, chimeric, single chain, $F_{ab}$ and $F_{(ab')2}$ fragments, and an $F_{ab}$ expression library or polypeptides engineered therefrom. Suitable antibodies include antibodies to well characterized receptors such as the transferrin receptor (TfR) and the epidermal growth factor receptor (EGFR) as well as antibodies to other receptors, such as for example the interleukin 4 receptor (IL-4R), the insulin receptor, CD30, CD34, and the CCK-A,B, C/Gastrin receptor. Additionally, the antibody is specific for mucin epitopes; glycopeptides and glycolipids, such as the Le$^y$-related epitope (which is present on the majority of human cancers of the breast, colon and lung); the hyaluronan receptor/CD44; the BCG epitope; integrin receptors; the JL-1 receptor; GM1 or other lipid raft-associated molecules; and $G_{D2}$ on melanomas. Tumor-specific internalizing human antibodies are also selected from phage libraries as described by Poul, et al. (J. Mol. Biol. 301: 1149-1161, 2000).

A cell surface ligand is a natural ligand or some synthetic analog adapted to be specific for an internalizing structure on the targeted cancer cells. Exemplary cell surface ligands include transferrin, epidermal growth factor, interleukins, integrins, angiotensin II, insulin, growth factor antagonist, β-2-adrenergic receptor ligands or dopamine releasing protein. For example, epidermal growth factor (EGF) is used to target the epidermal growth factor receptor (EGFR) or transferrin (Tf) is used to target the transferrin receptor (e.g. TfR and TfR2).

Suitable peptide cell targeting agents include peptide hormones such as oxytocin, growth hormone-releasing hormone, somatostatin, glucagon, gastrin, secretin, growth hormone (somatotropin), insulin, prolactin, follicle stimulating hormone or arginine-glycine-aspartic acid (RGD) peptides. Methods to identify peptides that bind to internalizing receptors and are internalized are known in the art (Hart, et al., J. Biol. Chem. 269: 12468-12474, 1994).

Targeting moieties include small molecules. A "small molecule" as used herein, is meant to refer to a composition that has a molecular weight of less than about 5 kD and most preferably less than about 4 kD. Small molecules are, e.g., nucleic acids, peptides, polypeptides, peptidomimetics, carbohydrates, lipids or other organic or inorganic molecules. For example, a small molecule is a hormone, such as estrogen, testosterone, and calciferol; folic acid or an analogue that binds to the folic acid receptor; nicotinic acetylcholine receptor agonists; or oligonucleotide receptor agonists.

In some embodiments the targeting agent is for example a compound that specifically binds to CD20, CD33, carcinoembryonic antigen (CEA), alpha fetoprotein (AFP), CA125, CA19-9, prostate specific antigen (PSA), human chorionic gonadotropin (HCG), acid phosphatase, neuron specific enolase, galacatosyl transferase II, immunoglobulin, CD326, her2NEU, EGFR, PSMA, TTF1, Muc, immature glycoslytaion, or an EMT marker. In preferred embodiments the targeting moiety is a antibody that specifically binds to CD20, CD33, carcinoembryonic antigen (CEA), alpha fetoprotein (AFP), CA125, CA19-9, prostate specific antigen (PSA), human chorionic gonadotropin (HCG), acid phosphatase, neuron specific enolase, galacatosyl transferase II, immunoglobulin, CD326, her2NEU, EGFR, PSMA, TTF1, Muc, immature glycoslytaion, or an EMT marker.

Molecular Imaging Probe Synthesis and Administration

In general, the molecular imaging probes can be prepared by coupling, for example, the optical imaging moiety to the targeting moiety by a covalent bond.

In some embodiments, the imaging moiety and the targeting moiety can each be coupled to a polymeric backbone.

In some embodiments, the imaging moiety is a precursor imaging moiety.

Molecular probes, precursor optical imaging moieties, and polymeric backbones can be obtained commercially or synthesized according to methods described herein and/or by conventional, organic chemical synthesis methods. The probes and probe intermediates described herein can be separated from a reaction mixture and further purified by a method such as column chromatography, high-pressure liquid chromatography, or recrystallization. As can be appreciated by the skilled artisan, further methods of synthesizing the probes and probe intermediates described herein will be evident to those of ordinary skill in the art. Additionally, the various synthetic steps may be performed in an alternate sequence or order to give the desired probes and probe intermediates. Synthetic chemistry transformations and protecting group methodologies (protection and deprotection) useful in synthesizing the probes and probe intermediates described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ea., Encyclopedia lo of Reagents for Organic Synthesis, John Wiley and Sons (1995), and subsequent editions thereof.

The probes of this invention include the probes themselves, as well as their salts and their prodrugs, if applicable. A salt, for example, can be formed between an anion and a positively charged substituent (e.g., amino) on a probe described herein. Suitable anions include chloride, bromide, iodide, sulfate, nitrate, phosphate, citrate, methanesulfonate, trifluoroaeetate, and acetate Likewise, a salt can also be formed between a cation and a negatively charged substituent (e.g., earboxylate or sulfate) on a probe described herein. Suitable cations include sodium ion, potassium ion, magnesium ion, calcium ion, and an ammonium cation such as tetramethylammonium ion. Examples of prodrugs include esters and other pharmaceutically acceptable derivatives, which, upon administration to a subject, are capable of providing active probe.

Pharmaceutically acceptable salts of the probes include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, 0 glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3 phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the probes and their pharmaceutically acceptable acid addition salts. Salts derived from appropriate bases include alkali metal (e.g., sodium), alkaline earth metal (e.g., magnesium), ammonium and N-(alkyl)4 salts. This invention also envisions the quaternization of any basic nitrogen-containing groups of the compounds disclosed herein. Water or oil-soluble or dispersible products may be obtained by such quaternization. Salt forms of the probes of any of the formulae herein can be amino acid salts of carboxy groups (e.g. L-arginine, -lysine, -histidine salts).

The term "pharmaceutically acceptable carrier or adjuvant" refers to a carrier or adjuvant that may be administered to a subject (e.g., a patient), together with one of the probes described herein, and which does not destroy the pharmacological activity thereof and is nontoxic when administered in doses sufficient to deliver a therapeutic amount of the probe.

Pharmaceutically acceptable carriers, adjuvants, and vehicles that may be used in the new methods include, but are not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as a-, it-, and y-cyclodextrin, or chemically modified 0derivatives such as hydroxyalkylcyclodextrins, including 2- and 3-hydroxypropyl-'B cyclodextrins, or other solubilized derivatives may also be advantageously used to enhance delivery of probes described herein.

Pharmaceutically acceptable carriers, adjuvants, and vehicles that are used are capable of locally increasing the osmotic pressure allowing the molecular imaging probe to difuse readily into the cells and tissue. For example, salts, like sodium chloride and potassium chloride, sugars, like dextrose, and other compounds such as sodium sulfate can be used as excipients to regulate osmotic pressure.

Additionally, the pharmaceutically acceptable carriers, adjuvants, and vehicles that are used are capable of modifying the local pH, ionic strength, as to enhance the activity of the target enzymes. For example, the pH of the buffer solution can be adjusted by using acids such as hydrochloric acid or bases such as potassium hydroxide. Buffers that adjust the pH and ionic strength include Bicarbonate, Boronate, and Phosphate buffers.

Optionally, the molecular imaging probe is formulated with a compound that allows the application location and eveness of the administration of the molecular imaging probe to be confirmed. For example, a UV dye or an additional fluorescent molecule is included in the formulation. Preferably, the UV dye or additional flurescent molecule has a different excitation and emission spectrum than the molecular imagng probe.

The probes and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg). The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970).

The compositions described herein may include any conventional non-toxic pharmaceutically-acceptable carriers, adjuvants or vehicles in addition to any of the probes described herein. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non toxic parenterally acceptable diluent or solvent, for example, as a solution in 1,3 butanediol. Among the acceptable vehicles and solvents that may be employed are mannitol, water, Ringer's solution and isotonic sodium chloride solution. In addition, sterile, fixed oils are conventionally employed as a solvent or suspending medium.

For this purpose, any bland fixed oil may be employed including synthetic mono- or 0 diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions described herein may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried cornstarch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions described herein may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions is useful when the desired treatment involves areas or organs readily accessible by topical application. For application topically to the skin, the compositions can be formulated with a suitable ointment containing the active components suspended or dissolved in a carrier.

Carriers for topical administration of the compounds include, but are not limited to, lo mineral oil, liquid petroleum, white petroleum, propylene glycol, polyoxyethylene polyoxypropylene compound, emulsifying wax and water. Alternatively, the compositions can be formulated with a suitable lotion or cream containing the active compound suspended or dissolved in a carrier with suitable emulsifying agents.

Suitable carriers include, but are not limited to, mineral oil, sorbitan monostearate, polysorbate 60, cetyl esters wax, cetearyl alcohol, 2-octyldodecanol, benzyl alcohol and water. The compositions can also be topically applied to the lower intestinal tract by rectal suppository formulation or in a suitable enema formulation. Topical transdermal patches are also included in this invention.

The compositions may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition optionally having the probe and an additional agent (e.g., a therapeutic agent or delivery or targeting agent) can be administered using an implantable device. Implantable devices and related technologies are known in the art and are useful as delivery systems where a continuous, or timed-release delivery of compounds or compositions delineated herein is desired. Additionally, implantable device delivery systems can be useful for targeting specific points of compound or composition delivery (e.g., localized sites, organs). See, e.g., Negrin et al., Biomaterials, 22(6):563 (2001). Timed-release technology involving alternate delivery methods can also be used in the new methods. For example, timed-release formulations based on polymer technologies, sustained-release techniques and encapsulation techniques (e.g., polymeric, liposomal) can also be used for delivery of the compounds and compositions delineated herein.

Imaging Systems

An imaging system useful in the practice of this invention typically includes three basic components: (1) an appropriate energy light source for imaging moiety excitation, (2) a means for separating or distinguishing emissions from energy source used for imaging moiety excitation, and (3) a detection system. This system could be hand-held or incorporated into other useful imaging devices such as surgical goggles or intraoperative microscopes.

In the imaging system, the field of view of each pixel will be one cell or a fraction of a cell. This will minimize signal background from autofluoresence from non-diseased (e.g. non-cancerous) molecules and will therefore improve the signal to noise ratio. The detector can be a charge-coupled device CCD, complementary metal-oxide semiconductor (CMOS), or avalanche photodiode (APD). An APD can detect weak optical signals due to the internal gain in the detector itself. Because the APD acts as a passively quenched circuit, when it detects single photons an electric field is generated that is sufficiently high to sustain the flow of an avalanche current. Other approaches that rely on external electronic amplification of a weak signal introduce a high background. Additional advantages of the APD include a high quantum efficiency and time resolution, which, if necessary, would allow us to temporally gate the detection and separate cell autofluorescence from probe fluorescence. Because the APDs can count single photons of light, they have the sensitivity to detect single cancer cells that have activated Prosense 750 or any other molecular probe. Indeed, others have created a solid-state microarray detector with APDs that can detect single molecules.

The imaging system will have a large depth of field making it less sensitive to small vibrations or motions made by larger macro-like motions of the handheld instrument. An image stabilization subsystem could be employed. Inertial sensor (gryo and accelerometer) would be placed on the hand held portion to detect motion and provide a compensation. The compensation could be moving the image sensor, or lens or employing digial image enhancement.

Preferably, the imaging system associates one cell with one or more pixels of a CCD, CMOS, or APD array such that the field of view of any pixel is one cell or less. This will maximize the photon flux rate (photons/sec-area) and minimize the background emission (auto fluorescence) which, along with the dark count, determines the signal/noise of the instrument and its sensitivity. If the field of view of a pixel contains several cells and only one is a cancer cell that has illuminated molecular imaging probes, the average photon flux rate to the pixel will be reduced and the ratio of the signal to background noise reduced. Furthermore, if multiple cancer cells are closely spaced the imaging system will still be able to differentiate individual cells.

Techniques for aligning a cell with a pixel are: direct or semi direct (a fiber optic transmission from the cell to array) contact or with a lens.

FIG. 1 shows a bundle of 1-10 micron fiber optics as the instrument head. The fibers may be contoured to match the application. The configuration shown would be used in analysis of crater surfaces. The fibers would transmit the laser excitation and the return fluorescence from the area of interest. Assuming a detector pixel array of 5 micron detectors spaced 5 microns apart and a typical cancer cell of 20 microns diameter then there would be about 4 pixels matched per cell. The fiber bundle could be 2-5 micron diameter fibers in this configuration. There will be some loss of signal from the following elements:

Fiberoptic transmission losses

View factor from cell to fiber-end (very small if the fibers are in contact with the tissue) and then again from fiber-end to the lens (which for the geometry below subtends 60/180 degrees), loss through the dichromatic mirror and finally lens losses.

The advantages of this configuration are that it uses standard components of an optical system arranged in a module and customized with a fiber-optic bundle.

Figure 3:
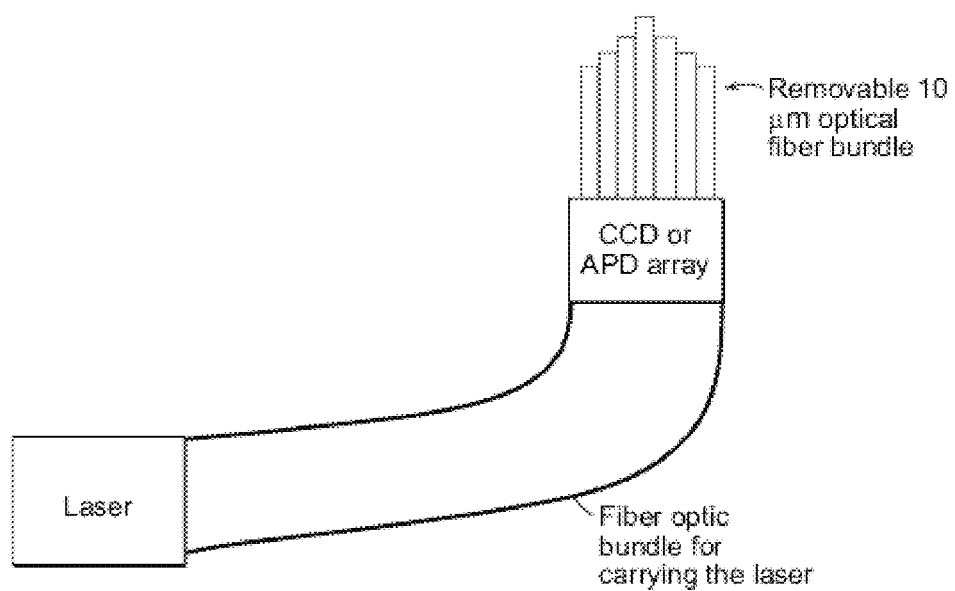
FIG. 3 is a schematic showing a remote laser of the imaging system according to the invention.
Figure 4:
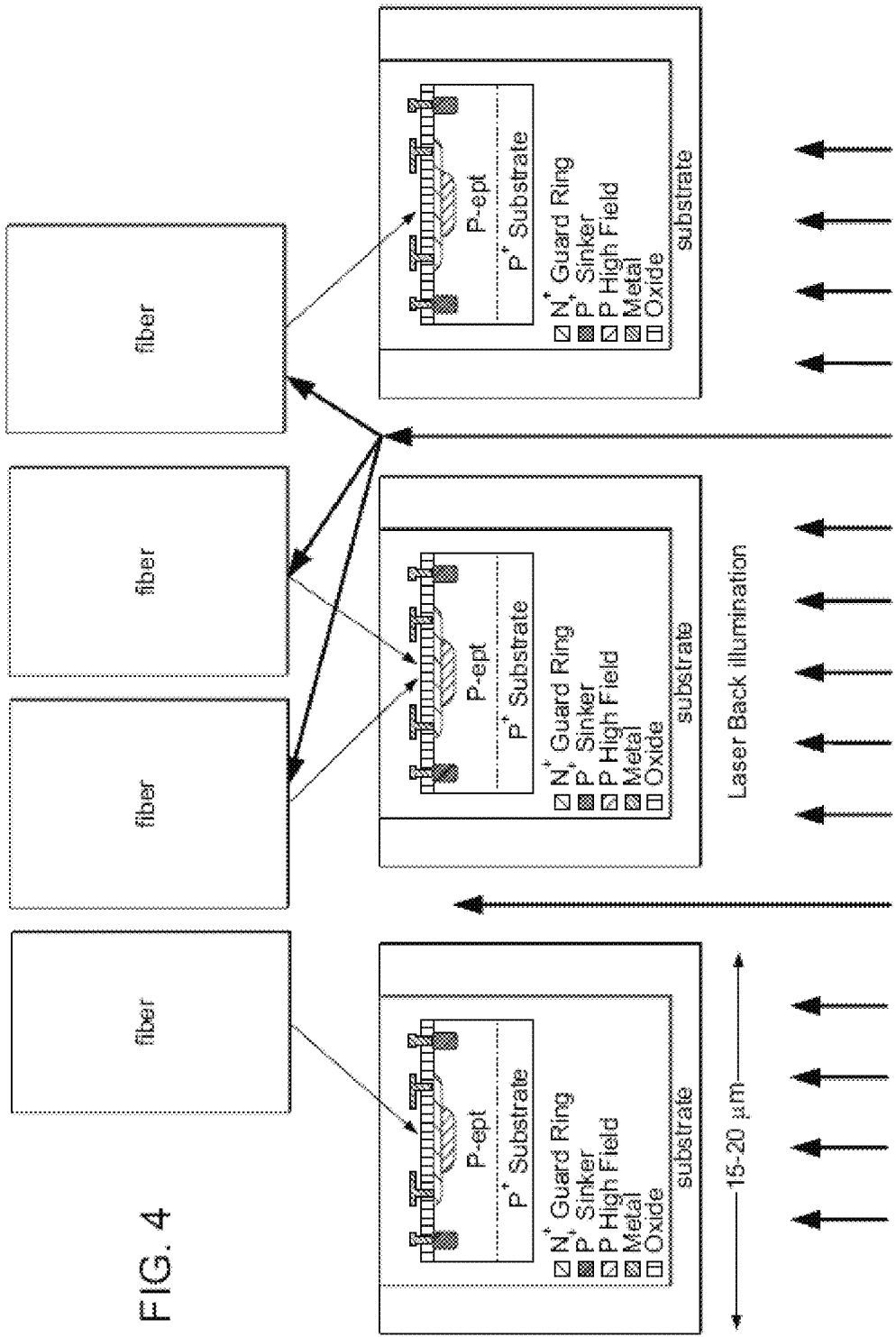
FIG. 4 is a schematic showing a backlite system of the imaging system according to the invention.

Another approach (FIG. 3) is to bring the detector in contact with the tissue or the fiber optic head. In this configuration, the array will need to consist of the detectors alternating with passages for the laser to come through or the laser will be brought to the imaging area via a separate fiber. FIG. 4 shows a possible configuration. The fibers are illuminated (dark lines) from the laser which goes through hole in the substrate. Depending upon the geometry each hole could illuminate 1 or more fibers. The CCD/APD is shown in a cavity, which limits the field of view of the detector. In this layout, each detector "sees" 2 fibers in this plane (perhaps 4 fibers in all depending upon the dimensions).

The choice between an APD, CMOS, or a CCD array for detection will depend upon the illumination and emission characteristics. The essential difference is that the APD can be run in Geiger mode to yield a very high sensitivity (one photon per second) if it is required. For instance, in the event that filters are used to eliminate backscatter from the laser pulse we may want the higher sensitivity of the APD.

There are a number of performance parameters that control the outcome which are on the biology side as well as the instrument.

The number of ligand reactions per second per cell together with the fluorescent duration (milliseconds) gives the number of possible florescent events per second per cell. The pulse rate should be as high as possible limited by the detector response time so as to maximize the photon generation from the molecular imaging probe.

The fiber bundle numerical aperture and, if necessary, associated lenses, will determine the acceptance angle of the molecular imaging probe light. Since the tip of the fiber bundle will not be in direct contact with the cancer cell that the molecular imaging probe has detected there will be a gap between the fiber tip and the cell of interest. This will widen the field of view of the fiber/pixel. A wider field of view (beyond a single cell) will adversely affect the sensitivity as the photon density (photon/sec-area) will be reduced and hence the sensitivity for detecting a single cancer cell will be reduced.

Figure 5:
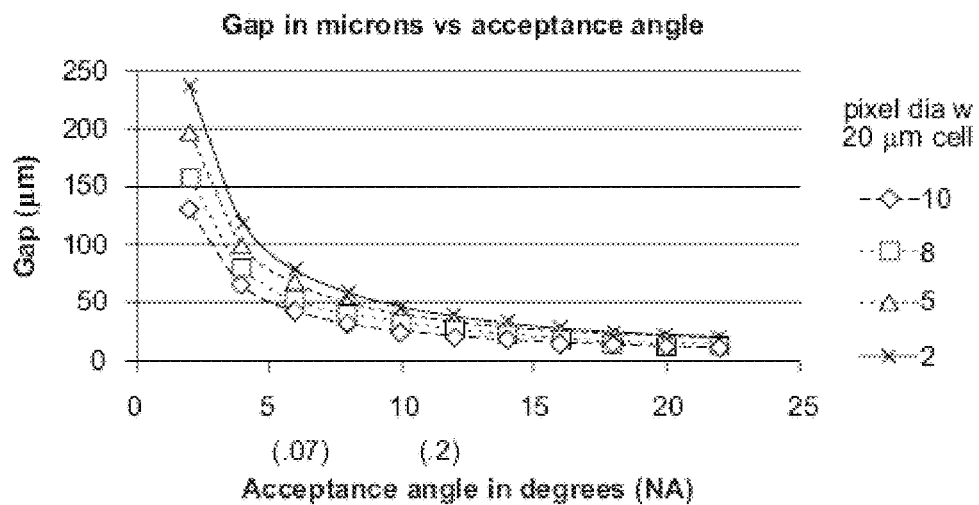
FIG. 5 is a graph showing gap vs. acceptance angle.

As seen in FIG. 5, allowable gap (from fiber end to the target cell) drops with increased acceptance angle. Typically the cancer cell of interest may be several layers beneath the surface 50-70 microns and there will also be some gaps between the surface tissue and the detector tip due to surface irregularities and thus a likely gap will be 100-200 microns. An acceptance angle of less than 5 degrees would be desirable but may not be practical. To accommodate the desire to limit the field of view of each pixel to a single cell a collimator may be used on the distal end of each bundle.

Preferred imaging systems to be used in the method of the present invention is described in the Figures.

Figure 6:
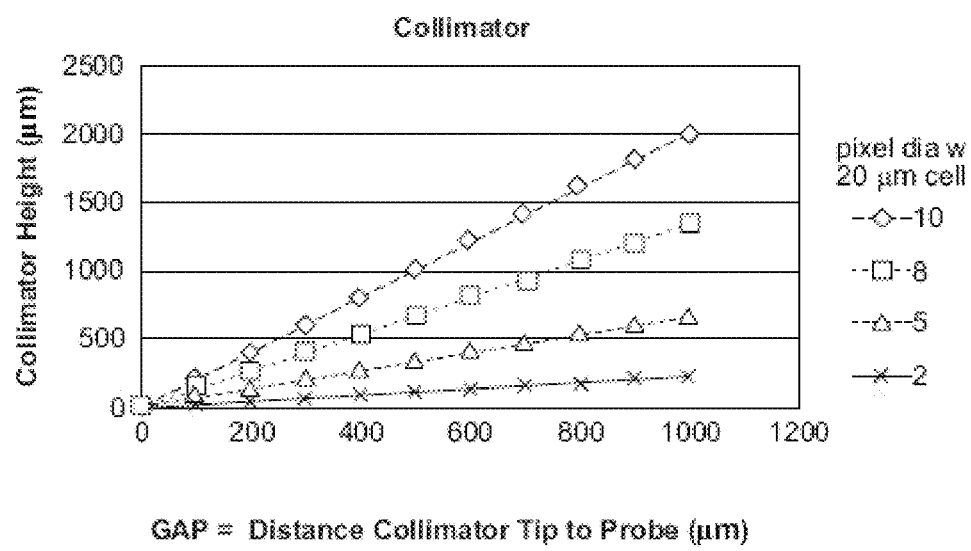
FIG. 6 is a graph showing collimator height in microns.

In FIG. 6 a collimator length can be selected for the application. As the pixel dia is reduced the collimator length is also reduced. For a 1000 micron gap a collimator of 200-500 microns in height would be appropriate.

Figure 14:
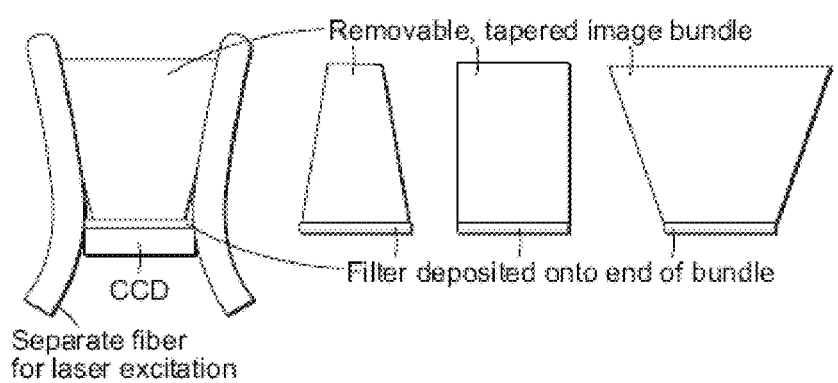
FIG. 14 is a schematic showing the tapered fiber bundle of the imaging system according to the invention.

Another approach, shown in FIG. 14, is to take a directly coupled removable, tapered, fiber bundle to a CCD camera on one end and the cells on the other end. The proximal end of the bundle would have an interference filter directly deposited on the fused silica so as to reject back scatter from the laser and emission outside the wavelength of the desired probe. The size of the proximal end would be chosen so as to directly match one fiber to one pixel of the CCD and, therefore, obtain optimum signal to noise. The size of the distal end would be chosen to map one cell onto one fiber. This size and taper could be adjusted to change the resolution of the device and could contain any of the features discussed above. By making the fiber bundle removable, variables such as field of view, resolution, and observed wavelength could be changed in the operating room as needed. In this modular design, the laser would be sent though a separate fiber, allowing for reduced backscatter and more easily changing the excitation wavelength if a different molecular imaging probe is utilized. Also, multiple CCDs could be hooked up to this device, further increasing the field of view.

Figure 15:
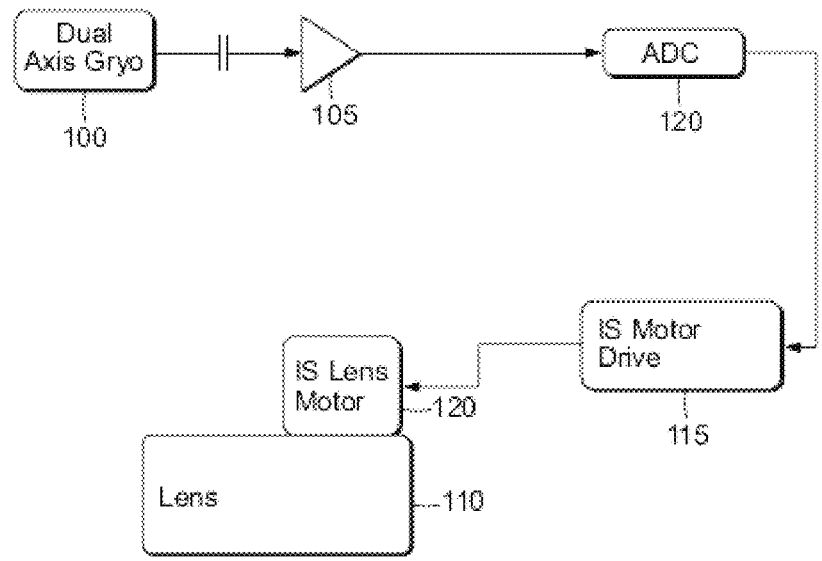
FIG. 15 is a schematic showing the image stabilization system of the imaging system according to the invention.

Under certain circumstances it will be desirable to maintain a relatively steady image of the field of view. An image stabilization system like those used in today's cameras could be used. FIG. 15 shows the general block diagram of the image stabilization system. In this configuration, a gyro is used to detect motion and the signal from the gyro is used to adjust the lens and maintain the image on the detector.

Figure 7:
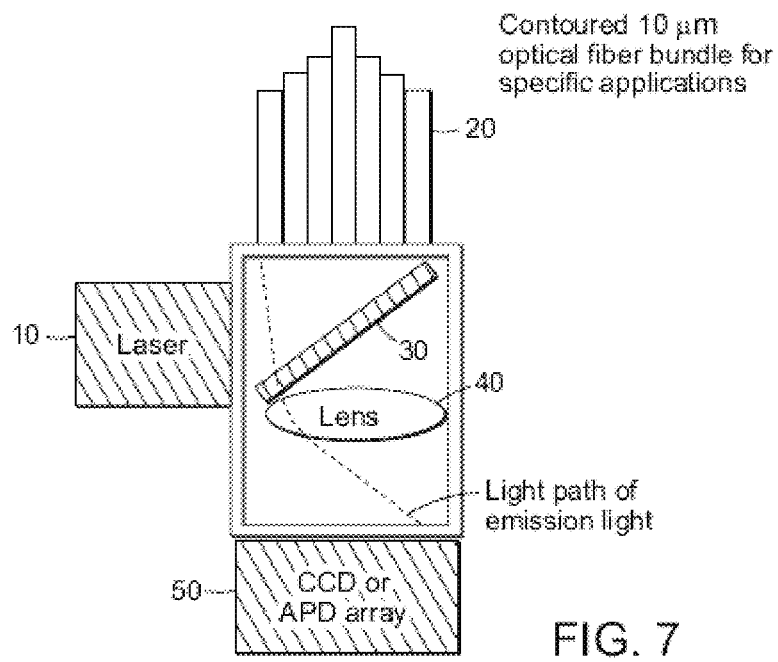
FIG. 7 is a schematic showing the imaging system according to the invention.

FIG. 7 shows the basis unit. A laser (10) is used to illuminate and stimulate the molecular imaging probes in the area of interest. Light from the laser (10) is reflected by the dichroic minor (30) to the base of the fiber optic bundle (20). The laser light is transmitted by the fiber optic bundle (20) to the tissue surface. The bundle (20) may actually be multiple bundles of different length creating a contoured surface to better match the tissue surface. The instrument will be used to inspect a resected area after surgery has removed the tumor.

Figure 8:
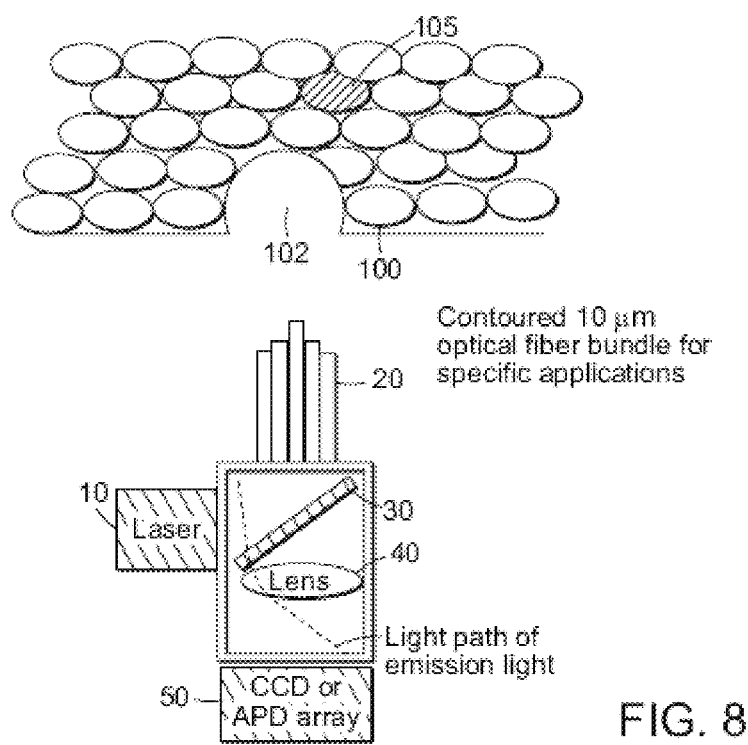
FIG. 8 is schematic showing the imaging system according to the invention and tissue (100) of the resected area.

A crater 1 cm to 5 cm may be the area of interest (102) as shown in FIG. 8. The contoured (20) fiber bundle is designed to conform with the resected area (102) providing intimate contact with the tissue in the detection of the cancer cell (105)

Light from a laser pulse excites the molecular imaging probe at the cancer cell (105) and emits light at a slightly different frequency. The emitted light form the molecular imaging probe on the cancer cell enters the fiber (20) bundle between laser pulses and travels back through the bundle to the dichroic minor (30). The returning light passes through the dichroic minor since it is a different wavelength than the laser whose light would be reflected by the mirror. The minor selectively passes the light returning from the molecular imaging proble. This lens is then projected on the CCD or APD array (50) by the lens (40).

Figure 9:
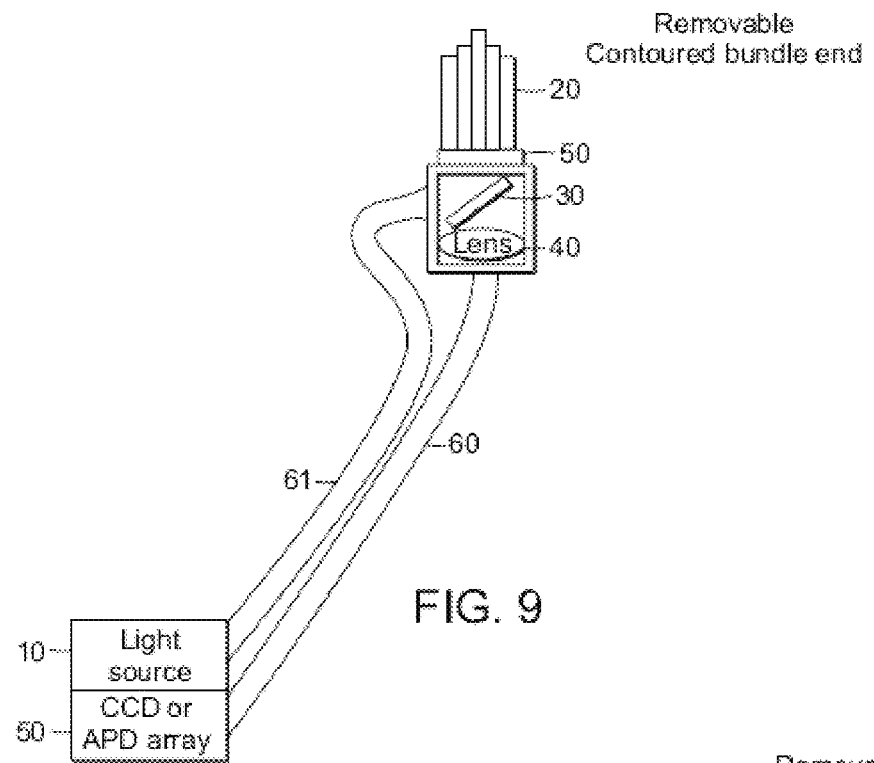
FIG. 9 is a schematic showing the remote light and detector of the imaging system according to the invention.

Another version of the instrument is shown in FIG. 9. In this configuration the light source (10) and the detector (50) are remote from the fiber bundle (20) and mirror (30) assembly to allow for easier handling of the detector. This is accomplished with additional fiber bundles. Fiber bundle (61) connects the light source to the minor assembly and bundle (60) connects the detector to the minor assembly.

Figure 10:
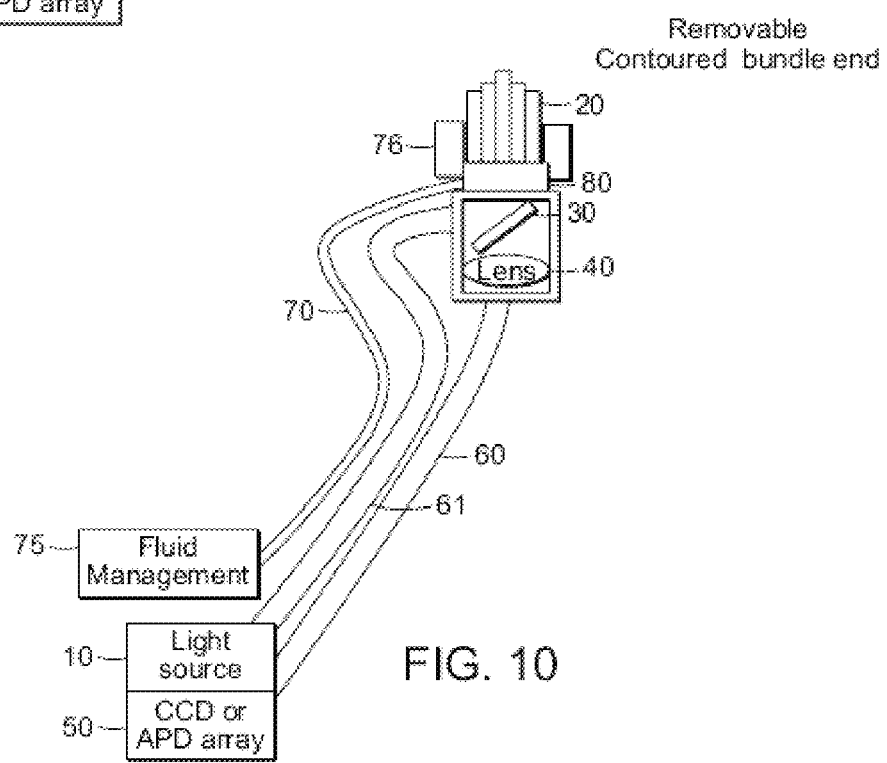
FIG. 10 is a schematic showing the integral fluid management system of the imaging system according to the invention.

FIG. 10 shows and integral fluid management system (75, 70, 76). The fluid management system can deliver or remove liquid, gas or vapor or and from the detection site. The purpose of the fluid management system is multifold. Tissue fluids (blood, serum, interstial fluids) can collect at the detection site. The fluids may scatter some of the emitted light from the molecular imaging probe thus limiting the sensitivity of the device. The fluid management unit (75) can draw these liquids away for the area with suction or push them away with an air wash. The suction or air wash would be pumped by the Fluid Management unit (76) through the connection tube (70) to the distribution unit (76) attached to the fiber bundle at the distal end. Another function of the fluid management system is to provide any reagents needed to conduct the assay. Local application of the molecular imaging probe may be appropriate in certain cases and the fluid management unit (75), connection tube (70) and distribution unit (76) would deliver reagent to the surface of interest.

Figure 11:
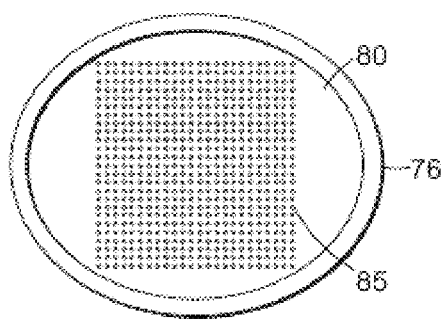
FIG. 11 is a schematic showing the fluid distributor of the imaging system according to the invention.

The distribution of the fluids at the distal end (76) is accomplished by a distributor (76). FIG. 11 shows a view of the distributor. Fluid (gas, liquid or vapor) is either drawn away or delivered to the target surface from the area (80) surrounding the fiber bundle (85) contained inside the distributor (76).

Figure 12:
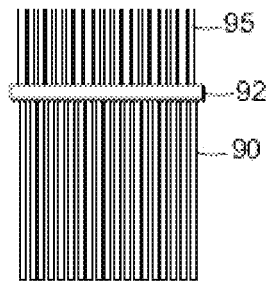
FIG. 12 is a schematic showing the collimator of the imaging system according to the invention.

A collimator may be needed to maintain the confined field of view of the pixels. FIG. 12 shows the cross-section of a collimator (95) attached to a thin end cap (92) on the end of the fiber bundle (90). The length and diameter of the collimator passages is determined by the desired optics.

Figure 13:
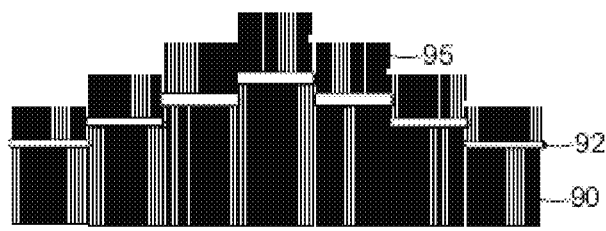
FIG. 13 is a schematic showing the contoured fiber bundle of the imaging system according to the invention.

A series of the fiber bundle/collimator units can be brought together to form the contoured end as shown in FIG. 13. In this figure fiber bundles (90) of different lengths are used to form the contoured end.

FIG. 15 shows an approach for image stabilization. A motion is detected by the gyro (100) the signal is amplified (105) and processed through and ADC (120) and DSP (not shown) and signals the image stabilization to power the lens motor and adjust the focus. These elements are all contained in the image stabilization module.

Figure 16:
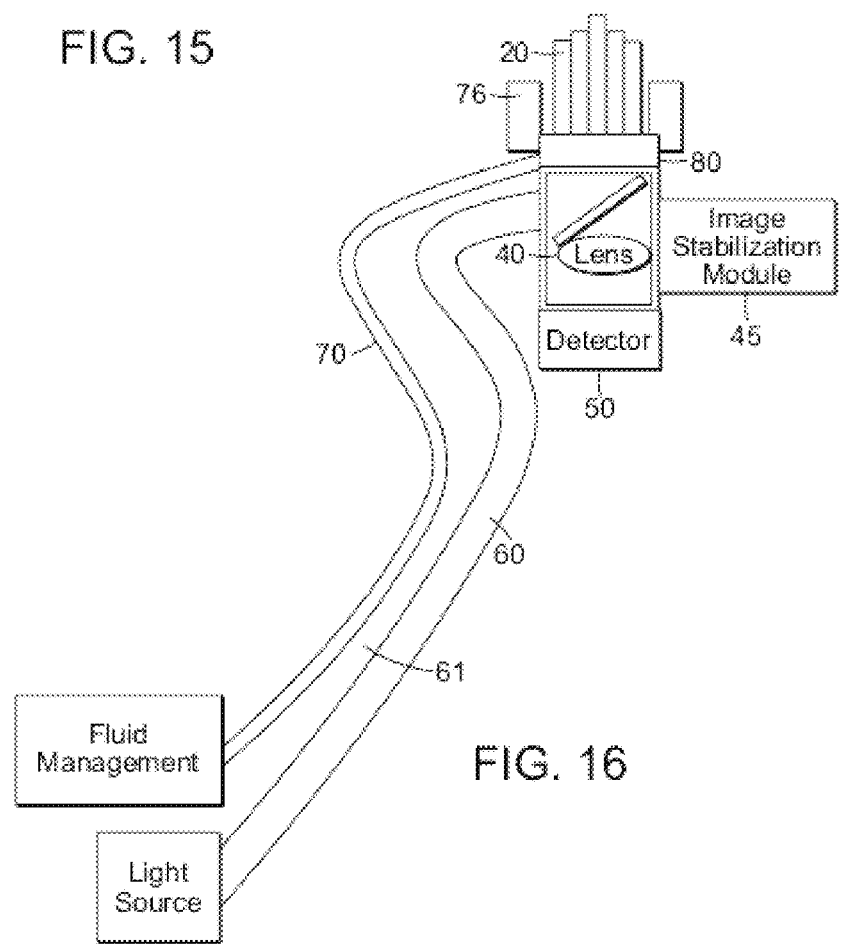
FIG. 16 is a schematic of the image stabilization integrated into the hand and held module of the imaging system according to the invention.

FIG. 16 shows the image stabilization module (45) integrated into the hand held unit to control the lens (40).

Figure 17:
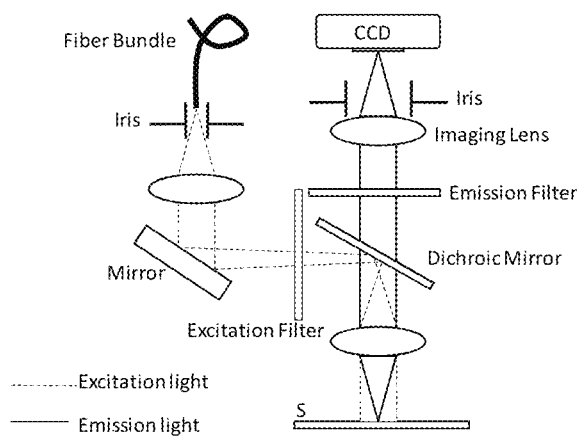
FIG. 17 is a schematic showing one embodiment of the imaging device using lenses to relay the image to a detector.
Figure 18:
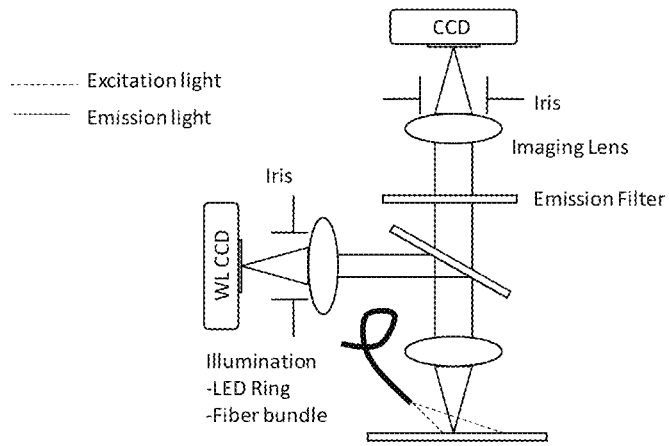
FIG. 18 is a schematic showing one embodiment of the imaging device to produce white light and fluorescence light images.

FIGS. 17 and 18 show examples of imaging systems without the use of fiber bundles at the distal tip. Instead lenses and filters are sufficient for imaging the abnormal cells.

EXAMPLES

Example 1

Design of a Delivery Device for Surface Application of Imaging Agent

The application mechanism must be able to handle efficiently and reproducibly the estimated small volumes (0.25 mL-1 mL) of molecular imaging probe Also, an even application coat is required for equal delivery of imaging agent throughout the tumor bed surface. For this application a manual, one-action pump to force the imaging agent solution through a venturi-type nozzle that will atomize the solution into small droplets for an even coating will be developed. The device will have a knob for the user to adjust the exit aperture size of the nozzle to increase or decrease the spray coverage area. A separate knob will be used to adjust the travel of the pump piston to increase or decrease the volume of imaging agent to be delivered.

Because of the presence of blood and other bodily fluids in the exposed tumor bed, visual confirmation that the imaging agent has been applied evenly and in the correct location may be difficult. To address this problem, the molecular imaging probe solution will contain an ultraviolet (UV) marker that will be delivered along with the molecular imaging probe. Using our device switching to a UV filter the surgeon can quickly scan the tumor area to ensure that the imaging agent solution was delivered properly. The UV marker will not interfere with the NIR emission of our imaging agent.

To characterize the application device, tissue phantoms made from PDMS or collagen will be sprayed with the device using our imaging agent. The evenness and reproducibility of the surface coating will be characterized by analyzing intensity profiles of images acquired via fluorescence imaging using the UV marker and different imaging agent concentrations.

Example 2

Optimization of Molecular Imaging Probe Formulation to Improve Diffusive Rate and Reduce Tumor Labeling Time The goal is to achieve tumor detection within five minutes after application of the imaging agent. The diffusivity of the molecular imaging probe will be modified by adding smaller and larger chains of a molecular carrier (polyethylene glycol). Another alternative is to embed the imaging agent in albumin, a well known carrier used for other molecules such as hormones, fatty acids and even drugs. A series of variants will be synthesized and tested for the formulation that provides the highest tumor-to-muscle signal ratio after five minutes of administration.

A potential problem is that the optimal diffusion rate required may not be achieved by only modifying the imaging agent molecular structure. To enhance the delivery of the imaging agent into the cells, the imaging agent will be administered in a solution that can change the osmotic pressure differential across the cell membrane. This will force water to rush into the cell and carry the imaging agent with it. The osmotic pressure differential will be adjusted by varying the concentration of salts (NaCl) in the solution.

Testing of the application method and different molecular imaging probe formulations will be done on surgical interventions in transgenic mice induced to develop soft tissue sarcomas in the rear leg. The gross tumor will be surgically resected while intentionally leaving partial tumor in the tumor bed as a positive control. The molecular imaging probe will be applied to the surface of the exposed the tumor bed (approximately 1 cm$^2$) in microgram doses. Each tumor bed and an area of healthy tissue will be imaged with the imaging device every 30 seconds to track the rate of change of fluorescence intensity. The goals of this test are (1) to empirically determine the relationship between tumor bed surface area and amount of molecular imaging probe required, (2) determine an optimal time point for imaging based on tumor-to-muscle signal ratio, (3) investigate and quantify differences in fluorescence intensity rates of change between tumor and healthy tissue.

Although wound healing problems due to the residual molecular imaging probe in the open wound are unforeseen because of the low doses being administered, the imaging protocol will indicate a simple but thorough wash over the open wound with clinical grade saline solution.

Example 3

Development of Several Complementary Algorithm Approaches for Intraoperative Identification of Cancer Cells All of the algorithms will provide fast image analysis (frame rates of at least 10 per second) to keep the image display feedback in real-time and reduce blurriness from handling the device to a minimum.

Our current algorithm (used with intravenous administrated imaging agent) sets an intensity-based threshold using fluorescence distributions between tumor and muscle. The algorithm has a calibration routine to set an intensity-based threshold to discriminate between tumor tissue and healthy muscle. We wish to take advantage of the dynamic characteristics of the surface application and propose to develop a new algorithm. The baseline will be established with a slice of resected tumor and a region of normal muscle. Then the imaging agent is applied onto a slice of resected tumor, the tumor bed and a portion of healthy tissue. After a predetermined time interval, the resected tumor and the portion of healthy tissue are imaged. The algorithm will analyze the fluorescence intensity distribution of both images pixel-by-pixel and will determine an appropriate intensity threshold to discriminate between tumor and healthy tissue based on the minimum fluorescence intensity from the tumor. Then, the tumor bed is imaged and each pixel value is compared against the threshold and a false color is assigned to those pixels above the threshold for visual recognition in the monitor display. The software will also provide audible feedback when a region with high residual fluorescence is imaged. The time in the operating room to calibrate the device is about 1 minute and full tumor bed scan in a human patient will take approximately 2 minutes.

We will evaluate time/signal signature of the muscle vs. cancer cells based upon the differential upregulation of cathepsins and differences in diffusion rates. The cathepsin family of enzymes have been shown to be upregulated in several types of cancer; therefore, it is expected that cancer cells will have a higher and faster activation of the molecular imaging probe than healthy muscle cells. In addition, because tumor tissue tends to be more "leaky" than healthy tissue, we anticipate that the molecular imaging probe will also diffuse into a cancer cell faster than into a muscle cell. The combination of these factors can lead into a measurable difference in the rate of change of fluorescence intensity between cancer and muscle cells—a signature of cancer cells. For this approach, the intensity of each pixel will be compared between consecutive images to establish the intensity rate of change in a pixel-by-pixel basis. The time intervals between images will be based on temporal data obtained. Statistical analysis will be used to group pixels following a similar trend in the rate of change of fluorescence intensity. Grouped pixels will be displayed in the monitor screen in false color for visual reference of their location. Using the fluorescence rates of change, discrimination between cancer and muscle will be performed. Because this approach requires tracking the intensity of pixels corresponding back to a specific location in the tumor bed through some period of time, a fiduciary marker, such as a surgical staple, can be placed in the tumor bed. This marker provides a reference for the imaging algorithm to align all the images for analysis. As an alternative, the device can be held in place temporarily using a surgical swivel arm.

Our third algorithm feature combines two independent means of discriminating cancer cells from healthy ones: imaging (imaging agent activation) and tissue autofluorescence. It is expected that the combination of both imaging techniques can have an additive result, yielding higher tumor-to-muscle signal. It has been shown that autofluorescence signals between tumor and healthy tissue are different although targeted molecular imaging has higher specificity and sensitivity. Our approach consists of taking an image of the tumor bed in the range of 450-550 nm wavelengths to get an autofluorescence footprint of the tumor bed. Then, an image in the (molecular imagng probe activation) of the exact same location will be recorded at the optimal imaging time point. The pixel values of the image will be normalized by the pixel values of the autofluorescence image. For example, if the image shows a 5:1 tumor-to-muscle ratio due to imaging agent activation and the autofluorescence signal ratio is just 2:1, the final effective contrast ratio between tumor and muscle is 10:1. For this approach, our imaging device will be outfitted with a motorized filter wheel to rapidly change optical filters for autofluorescence and imaging. Also, a fiduciary marker will be used for image alignment.

Before testing in mice, each algorithm will be validated first using in vitro models to simulate each scenario. For the first algorithm, to simulate relative fluorescence emission from tumor and muscle, phantoms made from PDMS or collagen will be coated with different concentrations of our optimized imaging agent and microspheres with calibrated emission will be used to simulate cells above and below the set threshold. To test the ability of the second algorithm to discriminate between different intensity rates of changes in the same field of view, two small reservoirs containing the same concentrations of imaging agent will be imaged simultaneously while two different amounts of cathepsin enzymes are added to each reservoir. This will generate different fluorescence rate of change between the two reservoirs, which can be adjusted by controlling the amount of cathepsins added to each well. For the third approach, phantoms similar to those generated to test the first algorithm will be prepared using fluorescent markers in the and 450 nm-550 nm wavelengths spectrum.

Example 4

In Vivo and Intraoperatively Testing the Imaging System in Sarcoma Surgeries in Mice For pre-clinical validation of the intraoperative imaging system, a cohort of n=42 mice with soft tissue sarcoma will be used as cancer specimens. The mouse study will consist of two arms, each with n=21 mice. From the first 9 mice tested, 3 will be assigned to each algorithm to compare their performance, before selecting the main algorithm candidate (a total of n=36 mice will be tested with the selected algorithm with 18 mice per arm). For both arms of the study, the gross tumor will be resected and the excised specimen will be analyzed post-surgery for positive margins by histopathology. Also in both arms of the study, the molecular imaging probe composition will be applied on the surface of the tumor bed and the tumor bed of each arm subdivision will be imaged to determine if there is "positive" or "negative" residual fluorescence. For all mice in arm A, the surgical wound will be closed without removing additional tissue. In arm B, if residual fluorescence is detected, it will be removed until the tumor bed is free of residual fluorescence. Then the surgical wound will be closed. All mice will be observed (search for palpable growth) for 120 days after surgery for local recurrence. The data collected for this aim will consist of fluorescence classification of the tumor bed by each algorithm, histology analysis of the resected tumor and local tumor recurrence.

Based on these results, three endpoints will be drawn for each algorithm: 1) to compare initial residual fluorescence detected by each algorithm with the pathological margin of the excised tumor (the current gold standard for cancer surgery) (n=36), 2) to determine whether local sarcoma recurrence in arm A (no additional tumor bed resection) correlates with residual fluorescence in the tumor bed (n=18), and 3) determine whether removing residual fluorescence in arm B (n=18) decreases the rate of local recurrence compared to the rate of recurrence in arm A (n=18) where no residual fluorescence is removed. The sensitivity, specificity, positive predictive value and negative predictive value will be characterized for each algorithm at every endpoint. A sample size of forty-two mice for this experiment was based on our experience where approximately 50% of the tumors recur after surgery. The goal of the validation is for the algorithm selected to obtain a sensitivity of 90% or better.

Example 5

Study of an Intra-Operative Imaging System for Ex-Vivo Margin Assessment of the Resected Human Breast Tumor Tissue The rate of secondary tumor surgeries due to a post-operative positive margin diagnosis for tumor lumpectomies can be as high as 50%. The proposed study aims to investigate an intra-operative method of ex-vivo tumor margin assessment to ensure negative margins are obtained, and thus, reduce the rate of secondary surgeries.

The intra-operative tumor margin assessment is performed by employing a fluorescence-based imaging system and an imaging device. After gross tumor excision, the surface of the resected tissue is sprayed with a molecular imaging probe in which fluorescence is activated by enzymatic action of overexpressed cathepsins in cancer cells. Five minutes after application, the tissue is examined for residual fluorescence using a wide-field, single cell resolution imaging device. Locations with high residual fluorescence are suspected to have cancer cells at the margin, thus, having a positive margin. Intraoperative diagnosis is compared to permanent H&E staining of the tissue by a pathologist.

Two different imaging agents are to be tested independently. Each imaging agent will be tested according the parameter matrix below:

| Buffer | pH | Application Temperature | Breast tumor samples |
|---|---|---|---|
| 100% DMSO | NA | Room temperature | 5 |
| | | 37° C. | 5 |
| 70% PBS, 30% DMSO | 6.0 | Room temperature | 5 |
| | | 37° C. | 5 |
| | 7.0 | Room temperature | 5 |
| | | 37° C. | 5 |

Protocol:
A. Pre-operative
  1. Imaging system is set up at the imaging location (OR) and is in stand-by mode.
  2. A sterile imaging tip is attached to the device.
  3. The device is covered with a sterile surgical drape.
  4. Imaging agent and spray application mechanism are readily available at the imaging location.

B. Intra-Operative
  1. The breast cancer patient undergoes a standard of care tumor resection surgery.
  2. After gross tumor is removed from the patient, a sample of the center of the resected tissue is removed via needle core procedure (positive control sample).
  3. The surfaces of the resected tumor and the needle core positive control are sprayed with the imaging agent using the airbrush mechanism at a dose of 10 µg per $cm^2$ of surface area.
    Data recorded: estimated tumor surface area and imaging agent required.
  4. After a five minute incubation period, the gross tumor surface is thoroughly washed with clinical grade saline solution.
    Data recorded: incubation time and amount of saline solution used for washing.
  5. The needle core tumor sample is imaged with the imaging device for positive control.
    Data recorded: fluorescence intensity level of needle core sample.
  6. The gross tumor is examined with the imaging device. Fluorescence intensity of gross tumor surface is compared to fluorescence intensity of positive control.
    Data recorded: save fluorescence images of resected tumor examination.
  7. Areas of high residual fluorescence in the gross tumor are marked (surgical staple, needle, etc.).
    Data recorded: take a picture of the resected gross tumor showing marks indicating areas of high fluorescence.

We claim:
1. An in-vivo method for spatially determining tissue heterogeneity in a subject comprising:
  (a) administering a composition comprising a molecular imaging probe with optical properties in the visible spectrum of 350-670 nm to the subject; and
  (b) obtaining an in situ image of said tissue, wherein the image allows for selective detection of one or more diseased cells within about 1 cm from the surface of the tissue and excludes deep tissue emission,
  wherein the molecular imaging probe has the following formula:
  $[S1]_i$-P-$[([S2]_j$-F)-A-$([S3]_k$-Q)-$[S4]_m]_n$ wherein the molecular imaging probe comprises at least one of the spacers S1, S2, S3, and S4, each independently comprising a group selected from PEG2, PEG2 attached to an amino acid, aminohexanoic acid, an amino acid sequence SRK, an amino acid D, and an amino acid C; i is 0 or 1; P is a pharmacokinetic modifier comprising a polyethylene glycol (PEG) or methoxyPEG molecule; F is a Cy5 fluorochrome; A is an amino acid sequence selected from GRKL or GGRK; Q is a QSY21 dark quencher; j is 0 or 1; k is 0 or 1; m is 0 or 1; and n is 1, 2, or 4.
2. The method of claim 1, wherein the probe is optimally imaged between 12 and 36 hours after administration.
3. The method of claim 1, wherein the probe is optimally imaged at less than 2 hours after administration.
4. The method of claim 1, wherein the image allows for selective detection of one or more diseased cells within about 5 mm from the surface of the tissue.
5. The method of claim 1, wherein the image allows for selective detection of one or more diseased cells within about 4 mm from the surface of the tissue.

6. The method of claim 1, wherein the image allows for selective detection of one or more diseased cells within about 3 mm from the surface of the tissue.

7. The method of claim 1, wherein the image allows for selective detection of one or more diseased cells within about 2 mm from the surface of the tissue.

8. The method of claim 1, wherein the image allows for selective detection of one or more diseased cells within about 1 mm from the surface of the tissue.

9. The method of claim 1, wherein the image is obtained using an imaging device wherein the field of view of each pixel is one cell or a fraction of a cell.

10. The method of claim 1, wherein the diseased cell is a cancer cell.

11. The method of claim 1, wherein the diseased cell is a central nervous cell, a cardiac cell, a bone cell, a tendon cell, or a muscle cell.

12. The method of claim 1, wherein the subject is a mammal.

13. The method of claim 12, wherein the subject is a human.

14. The method of claim 1, wherein the composition is administered systemically.

15. The method of claim 1, wherein the composition is administered topically in-vivo.

16. The method of claim 1, wherein the imaging probe comprises one or more fluorochromes and one or more dark quenchers.

17. The method of claim 1, wherein the molecular imaging probe has the following formula: PEG-SRK(Cy5)-GGRK(QSY21)-D.

18. The method of claim 17, wherein the PEG is between 500 g/mol and 100,000 g/mol.

19. The method of claim 17, wherein the PEG is about 2,000 g/mol.

20. The method of claim 1, wherein the molecular imaging probe has the following formula: C(PEG)-SRK(Cy5)-GGRK(QSY21)-D.

21. The method of claim 20, wherein the PEG is between 500 g/mol and 100,000 g/mol.

22. The method of claim 20, wherein the PEG is about 20,000 g/mol.

23. An in-vivo method for spatially determining tissue heterogeneity in a subject comprising:
(a) administering a composition comprising a molecular imaging probe with optical properties in the visible spectrum of 350-670 nm to the subject; and
(b) obtaining an in situ image of said tissue, wherein the image allows for selective detection of one or more diseased cells within about 1 cm from the surface of the tissue and excludes deep tissue emission,
wherein the molecular imaging probe has the following formula: [QSY21-Ahx-GGRK (Cy5)-PEG2-C]$_n$-PEG, wherein n=1, 2, or 4.

24. The method of claim 23, wherein the PEG is between 500 g/mol and 100,000 g/mol.

25. The method of claim 23, wherein the PEG is about 20,000 g/mol.

26. The method of claim 23, wherein the PEG is about 40,000 g/mol.

* * * * *